US 6,651,060 B1

(12) United States Patent
Harper et al.

(10) Patent No.: US 6,651,060 B1
(45) Date of Patent: Nov. 18, 2003

(54) METHODS AND SYSTEMS FOR RETRIEVAL AND DIGITIZATION OF RECORDS

(75) Inventors: Travis Kelly Harper, Sandy, UT (US); Benjamin Clark Stout, South Jordan, UT (US); Fred Bergstedt Schade, Jr., Highland, UT (US); Michael Glen Colemere, Alpine, UT (US); Matthew Doxey Cottrell, American Fork, UT (US)

(73) Assignee: Mediconnect.net, Inc., Sandy, UT (US)

(*) Notice: Subject to any disclaimer, the term of this patent is extended or adjusted under 35 U.S.C. 154(b) by 263 days.

(21) Appl. No.: 09/703,999

(22) Filed: Nov. 1, 2000

(51) Int. Cl.[7] .............................................. G06F 17/30
(52) U.S. Cl. ................................................ 707/9; 707/10
(58) Field of Search ................................. 707/1, 3, 9, 10

(56) References Cited

U.S. PATENT DOCUMENTS

| | | | |
|---|---|---|---|
| 3,920,895 A | 11/1975 | Vieri et al. ............ 358/426.07 |
| 3,920,896 A | 11/1975 | Bishop et al. ......... 379/100.13 |
| 3,958,088 A | 5/1976 | Vieri ..................... 379/100.13 |
| 4,739,377 A * | 4/1988 | Allen ......................... 355/133 |
| 4,817,050 A | 3/1989 | Komatsu et al. .............. 707/10 |
| 4,918,722 A | 4/1990 | Duehren et al. ....... 379/100.11 |
| 4,996,707 A | 2/1991 | O'Malley et al. ...... 379/100.13 |
| 5,068,888 A | 11/1991 | Scherk et al. .......... 379/100.11 |
| 5,084,769 A | 1/1992 | Miura ........................ 358/403 |
| 5,161,037 A | 11/1992 | Saito ......................... 358/468 |
| 5,164,899 A | 11/1992 | Sobotka et al. ................ 704/9 |
| 5,170,266 A | 12/1992 | Marsh et al. ............... 358/468 |
| 5,194,720 A * | 3/1993 | Reinnagel et al. .......... 235/437 |
| 5,267,303 A | 11/1993 | Johnson et al. ........ 379/100.07 |
| 5,340,966 A * | 8/1994 | Morimoto ................... 235/376 |
| 5,392,336 A | 2/1995 | Chang et al. .......... 379/100.11 |
| 5,408,619 A | 4/1995 | Oran .......................... 707/10 |
| 5,455,687 A | 10/1995 | Fukui et al. ................ 358/438 |
| 5,465,167 A | 11/1995 | Cooper et al. .............. 358/468 |
| 5,499,109 A | 3/1996 | Mathur et al. .............. 358/400 |
| 5,544,320 A | 8/1996 | Konrad ...................... 709/203 |
| 5,552,901 A | 9/1996 | Williams .................... 358/468 |
| 5,559,888 A * | 9/1996 | Jain et al. ................... 713/166 |
| 5,560,005 A | 9/1996 | Hoover et al. ................ 707/10 |
| 5,563,986 A | 10/1996 | Suzuki ...................... 358/1.15 |
| 5,579,393 A | 11/1996 | Conner et al. .............. 713/176 |
| 5,608,874 A | 3/1997 | Ogawa et al. .............. 709/246 |
| 5,659,164 A | 8/1997 | Schmid et al. .............. 235/375 |
| 5,664,109 A | 9/1997 | Johnson et al. ................ 705/2 |
| 5,696,901 A | 12/1997 | Konrad ...................... 709/203 |
| 5,699,526 A * | 12/1997 | Siefert ......................... 705/27 |
| 5,764,866 A | 6/1998 | Maniwa ..................... 358/1.15 |
| 5,768,581 A * | 6/1998 | Cochran ....................... 707/5 |
| 5,861,959 A | 1/1999 | Barak ........................ 358/403 |
| 5,867,821 A | 2/1999 | Ballantyne et al. ............ 705/2 |
| 5,890,129 A | 3/1999 | Spurgeon ...................... 705/4 |
| 5,892,214 A * | 4/1999 | Lindacher et al. ...... 235/462.32 |
| 5,903,889 A | 5/1999 | de la Huerga et al. .......... 707/3 |
| 5,911,776 A | 6/1999 | Guck ......................... 709/217 |
| 5,943,137 A | 8/1999 | Larson et al. ............... 358/403 |
| 5,963,966 A | 10/1999 | Mitchell et al. ............. 707/513 |

(List continued on next page.)

*Primary Examiner*—Jack M. Choules
(74) *Attorney, Agent, or Firm*—Workman Nydegger

(57) ABSTRACT

Process and system for locating, copying and sending requested records, such as medical records. The system includes a data processing center which acts as a central clearing house for processing the requests, requesters that generate the requests, and providers in possession of the requested records. The data processing center associates requests and related authorization forms generated by the requestor and transmits them to a provider in possession of the requested record. The provider then locates and copies the requested record and sends a copy of the record to the data processing center. The data processing center encrypts a digital copy of the requested medical record and sends it to the requestor. The communication linkages between the various parties advantageously include the Internet. A call center may be employed to ensure provider compliance with the request.

45 Claims, 11 Drawing Sheets

U.S. PATENT DOCUMENTS

| | | | |
|---|---|---|---|
| 5,974,444 A | 10/1999 | Konrad | 709/203 |
| 6,012,102 A * | 1/2000 | Shachar | 710/5 |
| 6,038,564 A * | 3/2000 | Sameshima et al. | 707/10 |
| 6,044,373 A * | 3/2000 | Gladney et al. | 707/10 |
| 6,061,146 A | 5/2000 | Mori | 358/403 |
| 6,073,106 A * | 6/2000 | Rozen et al. | 705/3 |
| 6,073,109 A | 6/2000 | Flores et al. | 705/8 |
| 6,112,986 A | 9/2000 | Berger et al. | 235/380 |
| 6,115,739 A | 9/2000 | Ogawa et al. | 709/215 |
| 6,154,738 A * | 11/2000 | Call | 707/4 |
| 6,171,112 B1 * | 1/2001 | Clark et al. | 434/322 |
| 6,314,425 B1 * | 11/2001 | Serbinis et al. | 707/10 |
| 6,351,813 B1 * | 2/2002 | Mooney et al. | 713/185 |
| 6,405,245 B1 * | 6/2002 | Burson et al. | 709/217 |
| 6,434,561 B1 * | 8/2002 | Durst et al. | 707/10 |
| 6,484,198 B1 * | 11/2002 | Milovanovic et al. | 709/218 |

* cited by examiner

METHODS AND SYSTEMS FOR RETRIEVAL AND DIGITIZATION OF RECORDS

BACKGROUND OF THE INVENTION

1. The Field of the Invention

The present invention relates to methods and systems for assisting a requester (e.g., an insurer) in rapidly obtaining medical records from a medical provider (e.g., a doctor). More particularly, the invention relates to methods and systems that employ a computer network which automatically processes and transmits a request and authorization for a medical record from a requestor to a provider and which subsequently receives, matches up, and forwards the medical record in electronic form to the requester.

2. The Prior State of the Art

There are various businesses and other entities that rely heavily on medical records to make business and other critical decisions. These include life insurance companies, property and casualty companies, personal injury attorneys, and patients, which may collectively be referred to as "medical record requesters." Medical records are typically generated by "providers," such as, doctors, hospitals, and independent diagnostic laboratories. There is, however, quite a disconnect between medical record providers and the aforementioned requestors such that actually filling a request for a medical record may take weeks or even months.

In a typical scenario for obtaining a medical record a requestor first determines which medical record from which provider is needed. Second, the person to whom the medical records pertain must fill out and send to the requestor a signed authorization form authorizing the provider to release the person's medical records to the requestor or representative. Third, the requestor sends the medical record request and signed authorization form to the provider. Fourth, the requester either relies on the provider to copy the medical record or sends someone to arrange to copy the requested medical records on the premises of the provider. Fifth, the provider must locate the requested medical record, the vast majority of which are in paper form and filed away in large filing rooms. Sixth, the medical record is photocopied. Seventh, the medical record is sent or otherwise delivered to the requestor. The foregoing process is cumbersome even when the requestor and provider are in close geographic proximity, sometimes even having an ongoing relationship. The process becomes exponentially more difficult when the requestor and provider are separated by large distances, particularly when the two parties do not have an ongoing relationship.

In many cases, doctors and other providers are slow to release medical records and often charge high rates in an attempt to recover what are, at best, the hassle costs of tracking down and providing medical records. This is particularly the case where the provider and requestor do not have an ongoing relationship and/or are separated geographically. In short, doctors and other providers are in the business of providing medical services and are not equipped and motivated to retrieve and provide medical records in a timely and efficient manner.

Likewise, the requestor is typically in the business of writing insurance policies, providing insurance coverage, or performing legal services. At best, obtaining medical records is a significant irritant. Worse, delays in obtaining medical records may mean lost sales to an insurance salesman, delay in processing loss claims, or inadequate or inefficient legal representation by a personal injury or defense attorney. Property and casualty insurers estimate that it costs about $25.00 per open claim per day. Life insurers often lose customers due to delays in being able to close deals and collect premiums. Notwithstanding the tremendous need to rapidly obtain copies of medical records, most requestors of medical records are typically not equipped to efficiently track down and retrieve medical records from the large number of potential providers, many of which have no ongoing relationship with the requester.

Because providers and requesters typically view medical record retrieval and copying to be, at best, an irritating facet of their respective businesses, third party copy services are often employed. Such copy services, in essence, bridge the communication and cultural gaps that separate disparate and essentially unrelated industries that would rather have nothing to do with each other but for the fact that one industry (the provider) produces a commodity (the medical record) that another industry (the requestor) needs but generally cannot generate on its own. While copy services may be better equipped and more willing to be the go-between and courier between requesters and providers, and whereas such services may actually be able to speed up the medical record retrieval and copying processes due to inherent economies of scale and expertise, such increases in efficiency are mostly marginal and do not address the more difficult systemic problems that work together to make the retrieval and copying of medical records an inherently time consuming and inefficient problem.

Aside from the foregoing problems and inefficiencies that presently plague requestors and providers in locating and sharing medical records, the rise of computers, more sophisticated telecommunications devices, facsimile machines, and the global computer network (i.e., the "Internet") show great promise and provide hope in generally increasing the efficiency of how businesses are run and how common and routine activities are carried out. The challenge, however, is implementation. Theoretical and predicted increases in efficiency in the business and manufacturing industries have not been realized and have often lagged behind the expectations of commentators and experts. This is due, of course, to the lack of workable systems that are able to efficiently and realistically implement an automation process. Different types of businesses commonly have very distinct cultures and methods of carrying out their day-to-day operations. More often than not, such differences do not easily lend themselves to quick and obvious automation procedures. For example, it would greatly increase the speed and efficiency of medical record retrieval if such records were electronically created and stored. Unfortunately, about 95% of all medical records are still in paper form and hand written.

In the industry of locating, copying, and providing medical records, there are a number of issues that must be addressed for a document retrieval system to be workable. These include, for example, maintaining the confidentiality of information in a person's records, ensuring that the copying of a particular record has been legally authorized, preventing the record from being available to or intercepted by unauthorized parties, correctly matching up a particular medical record with a particular request, and preventing unauthorized copying, alteration, or obliteration of data in the medical record. Simply requesting information via e-mail or other unsecured means over the Internet would not adequately address the foregoing concerns.

In short, it would be an advancement in the art of medical record retrieval to provide methods and systems which could greatly accelerate the retrieval process, while maintaining the confidentiality and security of the medical record.

SUMMARY OF THE INVENTION

The present invention encompasses medical record retrieval processes and systems, and software for implementing these processes, that greatly streamline the process of obtaining a medical record from a provider on behalf of a requestor. Typical requesters of medical records include life insurers, property and casualty insurers, and personal injury and defense attorneys. In many cases, obtaining a medical record is a condition precedent to entering into a contract, paying out a claim, or having sufficient evidence to prepare a legal case. The present invention greatly reduces the time in which a medical record may be obtained, thus reducing, e.g., monetary costs and lost business.

The processes and systems according to the present invention are advantageously implemented using a plurality of computers which communicate together, typically a computer network or system. In some cases, human assistance may be necessary to locate, process, and send certain data which is then further processed by means of one or more computers.

The inventive processes and systems that enable a requestor to obtain a medical record from a provider advantageously employ one or more centralized data processing centers, comprising one or more computers or computer systems, in communication with remote computers or computer systems employed by the various requesters. The data processing center is also in electronic communication with providers from whom a medical record is to be requested. To help ensure compliance, the data processing center may electronically communicate with one or more telephone calling centers that employ individuals assigned to contact a specific provider while that provider receives an electronic communication from the data processing center. The data processing center may also be in electronic communication with a data conversion device, such as a scanner or fax machine, used to convert a medical record, such as a paper-based medical record, into an appropriate electronic form.

The inventive processes and systems generally include four basic steps and subsystems. First, a request for a medical record and a proper authorization are electronically received from a requestor by a data processing center. Second, the data processing center electronically transmits the request and authorization to a provider. Third, the provider and/or a copy service locates, copies, and sends the requested medical record to the data processing center. Fourth, the data processing center matches up the medical record with the corresponding request, creates an encrypted copy of the medical record, and transmits the encrypted copy of the requested medical record to the requestor or other authorized party.

In the first step and subsystem, the initial request from the requestor to the data processing system is typically generated by means of a computerized request form using software designed to generate standard forms for that requestor. As the request form is generated, a request identification code, such as a serial number, is generated for each request. An authorization form is also generated together with a fax cover sheet or electronic form that includes the identification code. After the data processing center receives the request and authorization, it associates them together by comparing and finding a relationship between their respective identification codes. In a purely electronic system, the identification codes in both the request and authorization will advantageously be in digital text format and thus readily readable by a computer. However, in the present culture, people are used to, and often prefer, hand-signed authorization forms, thus requiring such forms to be faxed or otherwise converted into electronic form, typically as a graphic rather than a text file. To associate the identification code from an authorization fax cover sheet with a corresponding request, a bar code or other scannable image representative of the identification code may be used.

In the second step and subsystem, the data processing center transmits each request and authorization to the one or more providers having access to the requested medical record(s), together with a cover sheet for the medical record that includes the identification code. The data processing center may also transmit the request and authorization to a call center at or about the same time it transmits the request and authorization form to the provider. A designated individual within the call center then places a telephone call to, or otherwise initiates communication with, the provider, preferably to an individual in close proximity to the fax machine or other device that receives the request and authorization. Because it has been found that providers typically respond more readily to a request from a known person, it may be advantageous to assign a particular caller or small group of callers to a particular provider so as to create an ongoing relationship and associated goodwill between certain callers and certain providers.

In the third step and subsystem, the medical record is located, copied, and sent or faxed by the provider or copy service to the data processing center, together with the cover sheet. The cover sheet includes the identification code, typically in the form of a bar code or other scannable information, so that when the medical record and cover sheet are received by the data processing center the medical record can be readily associated with the request by means of comparing the respective identification codes of the cover sheet and request. Medical records are typically in paper form such that they must typically be scanned and converted into electronic form, e.g., as graphics files. This may be advantageously performed by means of a fax machine, such as a fax machine used to send the medical record from the provider to the data processing center. If the medical record is sent by the provider in paper form, the record will typically be scanned and thereby converted into digital, e.g., graphic, form. Medical records may also be received from the provider in electronic form, such as when records are stored by or for the provider in an electronic database. Character recognition software may alternatively be used to convert a medical record into a text file, at least in part.

In the fourth step and subsystem, the data processing center transmits an electronic or facsimile copy of the requested medical record to the requester or other authorized party. A computer can be used to match the medical record and associated identifier code with the original request, as a requestor may often generate multiple requests during a given time period. At some point during or subsequent to the conversion of the medical record into electronic form, the electronic record is advantageously encrypted as a protection against unauthorized access, copying, alteration, or obliteration of the record. If a medical record is sent by the data processing center as an encrypted electronic document, special encryption software, typically password protected software, will be needed to access the medical record, thus maintaining the confidentiality and security of the medical record.

The foregoing medical record retrieval process and system significantly increases the ease and efficiency by which a requestor may obtain a medical record from a provider. The decrease in time and effort required to obtain the medical record significantly decreases the cost associated with having to request and track the location of a medical record. It will also be readily appreciated that after a particular medical record has been converted into electronic form and stored within a searchable database, it may be accessed much more rapidly in the future by simply generating a new request and authorization which identifies the medical record. Because the medical records are encrypted, unauthorized third parties are thus prevented from obtaining, altering, copying, or obliterating the record. Of course, it is also within the scope of the invention to destroy the electronic copy of a medical record, if desired, to maximize confidentiality and protection of the information contained therein.

Another advantage of the inventive methods and systems is that they provide for the creation of an efficient intermediary that is able to bridge the technological and cultural gaps that presently separate requestors and providers. In doing so, the third party intermediary is able, through verbal communication and electronic means, to educate different sectors so that they may, over time, generate more harmonious record production and retrieval systems, thereby prompting an evolution in greater systemic efficiency. For example, the present methods and systems may encourage providers to create electronic copies of medical records to facilitate the transfer of such records to requesters, thus reducing the time providers must typically spend in tracking down and retrieving medical records in tangible form. As the inventive medical record retrieval systems of the present invention proliferate, it will certainly be the case that other industries specializing in data scanning and conversion of paper records into electronic form may enter the scene and revolutionize the manner in which providers generate and store medical records.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth below.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

I. INTRODUCTION AND DEFINITIONS

Figure 1:
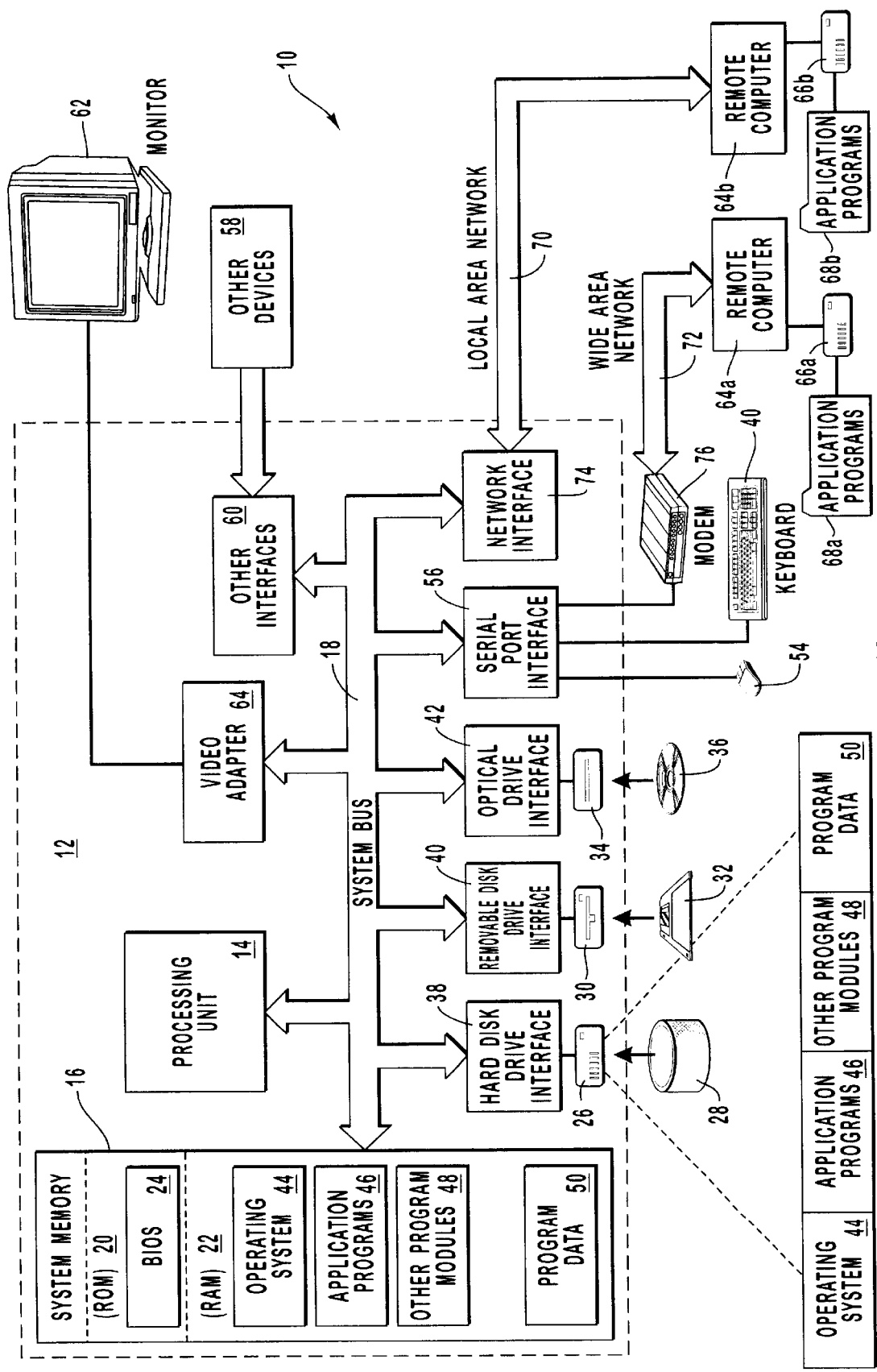
FIG. 1 illustrates an exemplary system that provides a suitable operating environment for the present invention.

The present invention relates to processes and systems for requesting and obtaining copies of medical records, as well as software for implementing these processes. Such processes and systems greatly streamline the ability to obtain a medical record from a provider on behalf of a requestor. The process and systems according to the present invention are advantageously implemented using a set of computers which communicate together, typically a computer network or system. Such communication may be by direct link, by the Internet, or a combination thereof. Some of the tasks may require human assistance to locate, process, and send certain information, which is then further processed by means of the computer network, typically a data processing center.

The term "data processing center" shall refer to a computer system that is essentially a computerized clearing house for receiving and processing requests for a medical record, communicating the requests to one or more providers, receiving digital copies of the requested medical records, and then sending copies of the records to one or more parties authorized to receive the records. The data processing center may be located at a single location or constitute a system of computers at different locations that are networked together. While preferably computerized and automated as much as possible, the functions carried out by the data processing center may require some human intervention.

The term "requestor" shall refer to any party that is making a request for a medical record through the data processing center. Examples of typical requesters include life insurers, property and casualty insurers, worker's compensation insurers, long term care insurers, personal injury and defense attorneys, health care providers, document copy services, providers of Internet services to insurers and attorneys, and government agencies. There is, however, no restriction as to who may constitute a "requestor". Thus, the requestor may be the party actually making the request, or an employee, agent, or affiliate of the requesting party.

The term "provider" shall refer to any individual or entity that may possess a requested medical record. Examples of providers include hospitals, health maintenance organizations, medical clinics, laboratory information systems, independent laboratories, doctors, nurses, doctor's assistants, and employees, agents, and affiliates of these individuals or entities. Examples of agents and affiliates include document repositories, copy centers, runners, communications centers and the like.

The term "access to", in the context of a provider having "access" to a medical record, shall refer to any situation in which a provider has or may obtain access to a requested medical record. Access may be actual or prospective.

The terms "identify" or "identifying", as in the data processing center identifying a provider having access to a requested medical record, includes simply reading the name of the provider within the request as well as independently identifying the provider by some other means.

The term "record" shall refer to one or more documents, whether in tangible or digital form, including hand written or typed records, such as hand written or typed medical records. Hence, the term "requested record" may include more than one physical document and/or more than one type or category of record.

II. SYSTEMS FOR REQUESTING AND PROVIDING DIGITAL COPIES OF MEDICAL DOCUMENTS

A. Basic Operating System.

The present invention extends to methods and systems for requesting, obtaining and providing digital copies of medical records. By way of general background, the embodiments of the present invention may comprise or be implemented, at least in part, using special purpose or general purpose computers including various computer hardware, as discussed in greater detail below.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media may include random access memory (RAM), read only memory (ROM), electrically erasable programmable read only memory (EEPROM), compact disc read only memory (CD-ROM), digital video disc (DVD), or other optical disk storage, magnetic disk storage or other magnetic storage devices, or any other medium which can be used to carry or store desired program codes in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium, as would be any medium for transmitting a propagated signal. Combinations of the above should also be included within the scope of computer-readable media. In addition to computer-readable media, computer-executable instructions or data structures may be partly or wholly provided to or sent from a computer in the form of a propagated wave, typically by means of one or more communications connections between two or more computers. Computer-executable instructions comprise, for example, instructions and data which cause a general purpose computer, special purpose computer, or special purpose processing device to perform a certain function or group of functions.

FIG. 1 and the following discussion are intended to provide a brief, general description of a suitable computing environment in which the invention may be implemented. Although not required, the invention will be described in the general context of computer-executable instructions, such as program modules, being executed by computers in network environments. Generally, program modules include routines, programs, objects, components, data structures, etc., that perform particular tasks or implement particular abstract data types. Computer-executable instructions, associated data structures, and program modules represent examples of the program-code means for executing steps of the methods disclosed herein. The particular sequences of such executable instructions or associated data structures represent examples of corresponding acts for implementing the functions described in such steps.

Those skilled in the art will appreciate that the invention may be practiced in network computing environments with many types of computer system configurations, including personal computers (PCs), hand-held devices, multi-processor systems, microprocessor-based or programmable consumer electronics, networked PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

With reference to FIG. 1, an exemplary system for implementing the invention includes a general purpose computing device in the form of a conventional computer system 10, which, in its broadest sense, includes components hardwired or otherwise associated together within a conventional computer box, bundle, or subsystem illustrated by item number 12, together with user interface, communications, and other devices and features located externally to, physically separated from, or otherwise spaced apart relative to the computer bundle or subsystem 12. By way of example, and not limitation, a conventional computer bundle or subsystem 12 includes a processing unit 14, a system memory 16, and a system bus 18 that couples various system components including the system memory 16 to the processing unit 14. The system bus 18 may be any of several types of bus structures including a memory bus or memory controller, a peripheral bus, and a local bus using any of a variety of bus architectures. The system memory includes read only memory (ROM) 20 and random access memory (RAM) 22. A basic input/output system (BIOS) 24, containing the basic routines that help transfer information between elements within the computer system 10, such as during start-up, may be stored in ROM 20.

The computer system 10, typically the computer bundle or subsystem 12, may also include a magnetic hard disk drive 26 for reading from and writing to a magnetic hard disk 28, a magnetic disk drive 30 for reading from or writing to a removable magnetic storage device 32, and an optical disk drive 34 for reading from or writing to a removable optical disk 36 such as a CD-ROM, digital versatile disk, a laser disk, or other optical media. The magnetic hard disk drive 26, magnetic disk drive 30, and optical disk drive 34 are connected to the system bus 18 by a hard disk drive interface 38, a magnetic disk drive-interface 40, and an optical drive interface 42, respectively. The drives and their associated computer-readable media provide nonvolatile storage of computer-executable instructions, data structures, program modules, and other data for the computer 10. Although the exemplary environment described herein employs a magnetic hard disk 28, a removable magnetic disk 32, and a removable optical disk 36, other types of computer readable media for storing data can be used, including magnetic cassettes, flash memory cards, Bernoulli cartridges, RAMs, ROMs, and the like. For purposes of the specification and the appended claims, the term "computer readable medium" may either include one or a plurality of computer readable media, working alone or independently, so long as they singly or collectively form part of a recognizable system for carrying out the processes of the invention.

Program code comprising one or more program modules may be stored on the hard disk 28, magnetic disk 32, optical disk 36, ROM 20, or RAM 22, including an operating system 44, one or more application programs 46, other program modules 48, and program data 50. A user may enter commands and information into the computer bundle or subsystem 12 by means of a keyboard 52, a pointing device (e.g., "mouse") 54, or other input devices (not shown), such as a microphone, joy stick, game pad, satellite dish, scanner, video player, camera, or the like. These and other input devices are often connected to the processing unit 14 through a serial port interface 56 coupled to the system bus 18. Alternatively, these and other devices 58 may be connected by other interfaces 60, such as a parallel port, a sound adaptor, a decoder, a game port or a universal serial bus (USB). Nonexhaustive examples of "other devices 58" include scanners, bar code readers, external volatile and nonvolatile memory or storage devices, audio devices, video devices, and microphones. A monitor 62 or another display device is also connected to the system bus 18 via an interface, such as a video adapter 64. In addition to the monitor 62, computers typically include other output devices (generally depicted as "other devices 58"), such as speakers and printers.

The computer system 10 may operate in or involve a networked environment using logical connections to one or more remote computers, such as remote computers 64a and 64b. Remote computers 64a and 64b may each be another personal computer, a server, a router, a network PC, a peer device or other common network node, and typically include many or all of the elements described above relative to the computer system 10, although only memory storage devices 66a and 66b and their associated application programs 68a and 68b have been illustrated in FIG. 1. The logical connections depicted in FIG. 1 include a local area network (LAN) 70 and a wide area network (WAN) 72 that are presented here by way of example and not limitation. Such networking environments are commonplace in office-wide or enterprise-wide computer networks, intranets, and the global computer network or "Internet".

When used in a LAN networking environment, the computer bundle or subsystem 12 is connected to the local network 70 through a network interface or adapter 74. When used in a WAN networking environment, the computer bundle or subsystem 12 may include a modem 76, a wireless link, or other means for establishing communications over the wide area network 72, such as the Internet. The modem 76, which may be internal or external, is typically connected to the system bus 18 via the serial port interface 56. In a networked environment, program modules depicted relative to the computer bundle or subsystem 12, or portions thereof, may be stored in a remote memory storage device (e.g., remote storage devices 66a and 66b). It will be appreciated that the network connections shown are exemplary, and other means of establishing communications over wide area network 72 may be used.

Although computer components are commonly arranged in the form depicted in FIG. 1, with some components of the computer system 10 physically located within, and other components physically located outside, the computer bundle or subsystem 12, it will readily be appreciated that the terms "computer" and "computer system" should be broadly understood to include any or all of the foregoing components in any desired configuration which facilitate carrying out the inventive methods and systems disclosed herein. The terms "computer" and "computer system" may therefore include other common features or components not depicted in FIG. 1.

In addition to the foregoing computer system, the inventive networks may include components such as fax machines, scanners, printers, copy machines and any other device or component that may be necessary to facilitate the retrieval and copying of the requested medical records. One level of human intervention may also be necessary to process or carry out certain steps such as entering into a transaction between the requestor and the person authorizing the release of the medical records, signing of the authorization form by the client or other authorized person, one or more agents of the provider who receives and processes the request for the medical record, and the person who ultimately reviews the medical record to determine whether the transaction dependant on the medical record should go forward. To help ensure compliance, one or more calling centers in communication with the data processing center may be assigned the task of initiating a personal communication, such as a telephone call, with a representative of the provider that has access to the requested medical record. In short, the exemplary descriptions of computer systems and other hardware are given by way of example only and not by limitation.

B. The Data Processing Center.

The systems according to the present invention for requesting, obtaining, and providing copies of medical records are controlled or directed by one or more data processing centers in communication with one or more requestors of medical records, one or more providers of medical records, and, optionally, one or more call centers. The centralized function or role of the data processing center according to the present invention is illustrated in FIG. 2.

Figure 2:
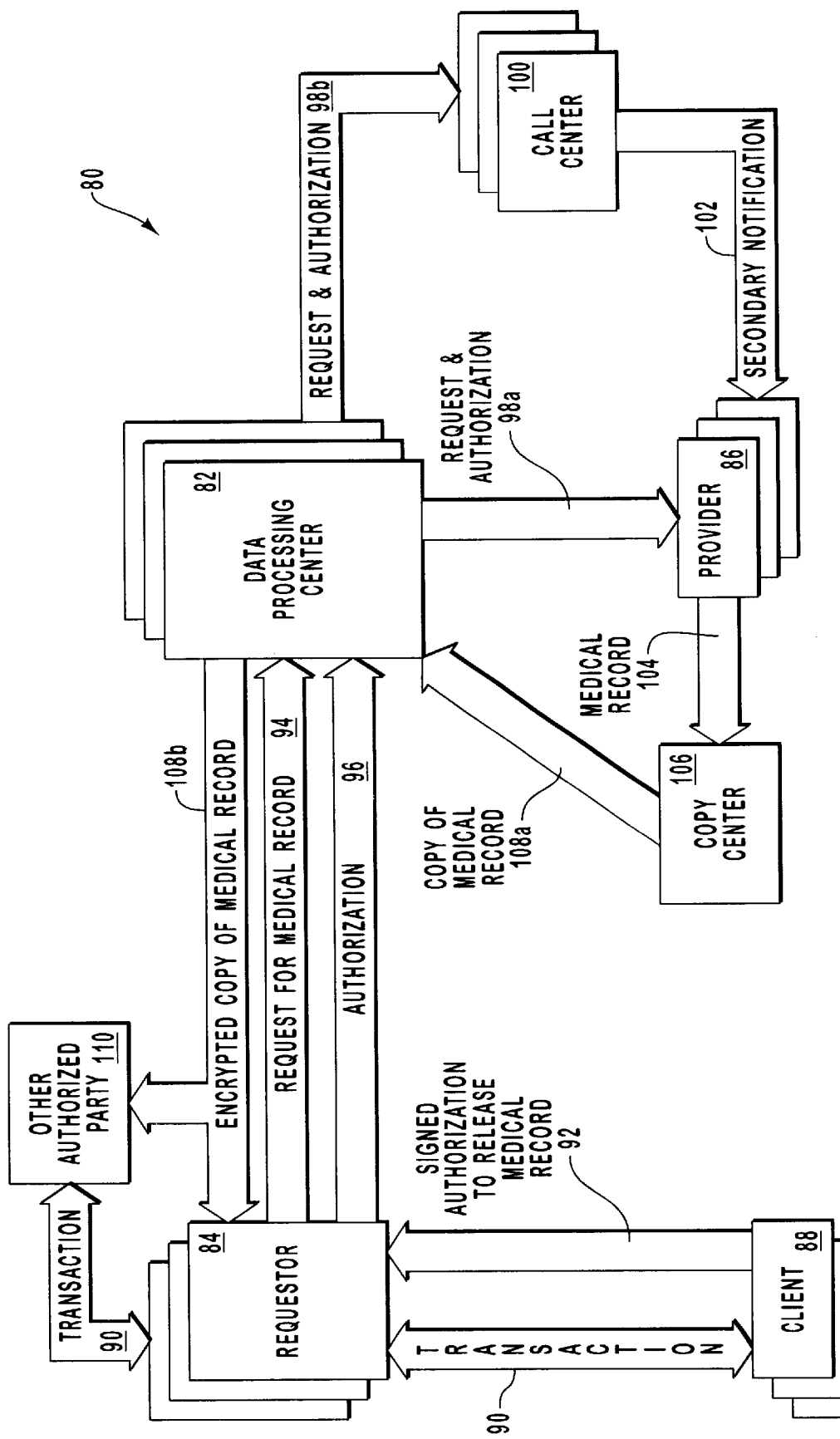
FIG. 2 is a schematic diagram illustrating an exemplary system or network for processing requests for medical records according to the invention.

As depicted in FIG. 2, a system for processing requests for medical records according to the present invention includes, as its main information and control hub, one or more data processing centers 82. The data processing center 82 is substantially or wholly automated by means of one or more computer systems that are able to receive and analyze information, make decisions, and send information as needed to carry out the processes disclosed herein. The data processing center 82 is in communication with one or more requestors 84, and one or more providers 86. The data processing center 82 may include any hardware peripheral to the computer system that will facilitate the process of requesting, obtaining, and providing copies of requested medical records. The data processing center 82 may involve human intervention to carry out one or more of the tasks described herein.

In a typical scenario, a client 88 of requestor 84 enters into a transaction 90 which requires the obtaining, review, and analysis of one or more medical records pertaining to the client 88 and/or transaction 90. For the requestor to have permission to obtain one or more medical records of the client 88, the client provides a signed authorization 92 which authorizes the release of the one or more medical records. The requestor also generates a request 94 for medical records and sends the request 94 and a digitized version 96 of the signed authorization 92 to the data processing center 82. The means for generating and sending the request and authorization will typically include a computer and one or more optional devices such as a printer, an electronic signature device, a fax machine, a scanner and the like.

The request is typically generated and sent in electronic form, such as in the form of a hypertext markup language (HTML) document or by means of an application program interface (API), discussed more fully below. The authorization 92 may either be digitally signed, and therefore in digital form from the outset, or it may be a manually signed document that is scanned, digitized, and sent as a graphic file from the requestor 84 to the data processing center 82 (e.g., by means of a fax machine).

The data processing center 82 includes means for associating each request 94 with its corresponding authorization 96, typically a human or electronic processor that compares identification codes of each. The means for associating each request 94 with its corresponding authorization 96 may include a bar code reader together with algorithms for accurately relating the bar code with the identification code represented by the bar code. The request 94 and authorization 96 are bundled together and sent to the provider 86 as a bundled request and authorization 98*a*, and optionally to a call center 100 as a bundled request and authorization 98*b*.

The means of the provider 86 for receiving the bundled request and authorization 98*a*, or one or more of the individual components thereof, may include one or more fax machine, telephones, computers, hand-held telecommunications devices, or other communication receiving means. At present, a typical means for receiving the request and authorization 98*a* is a fax machine, together with a telephone for optional receipt of a telephone call from the call center 100. In order to streamline the process by which the data processing center 82 is able to communicate or transmit the request and authorization 98*a* to the provider 86, a provider interface module may be advantageously employed. The provider interface module allows a provider 86 to log in on a regular basis and determine if and what records have been requested through the data processing center 82. This potentially eliminates the need for phone calls from the call center 100 and the need to sort through a number of unrelated faxes to see which pertain to requests for medical records.

The call center 100 may include one or more fax machines, computers, telephones, or other means for receiving the request and authorization 98*b* from the data processing center 82. The call center 100 typically employs a number of individuals who are assigned the task of providing secondary notification 102 to each provider 86 to ensure compliance of the request 94 by the provider 86. The call center advantageously includes a computerized system for assigning each request to a particular individual caller, preferably one having a preestablished relationship with the provider 86 to which the request 94 has been or will be sent. Of course, it is certainly within the scope of the invention to provide any system that assigns any caller to any particular provider as desired.

The provider 86 typically includes or has access to a storage facility that houses the medical records generated by the provider or affiliate, including the requested medical record 104. In the majority of cases, the requested medical record 104 will be in tangible form and stored within conventional files within a conventional filing cabinet or system. Nevertheless, it is believed that as the automation process provided by the present invention becomes more widespread that substantial numbers of electronic copies of medical records may begin to be stored in a searchable digital database. A searchable database would allow the provider 86, or even the data processing center 82, to directly search for a requested medical record while dispensing with many of the foregoing intermediate steps. Of course, for the data processing center 82 to have legal authority to search a database of the provider 86, the provider 86 may have to grant authorization, either on a case-by-case basis or as part of an ongoing agreement with the data processing center 82 or affiliate.

Regardless of the form of the medical record 104, the record 104 is copied, either in tangible or digital form, such as by means of a copy center 106. The copy center 106 may include photocopy machines, scanners, fax machines, or other hardware capable of making and sending a tangible or digital copy 108*a* of the requested medical record 104.

In the case where the copy 108*a* of medical record 104 is a tangible copy (e.g., a photocopy), it will be converted into digital form at some point within the system, either by the copy center 106, the data processing center 82, or some other third party (not shown), such as an affiliate of the data processing center 82. The network 80 will therefore include digitizing means for converting a tangible record into digital form, such as a scanner or fax machine.

The data processing center 82 will advantageously include a processing system and associated software for converting a digitized copy of the medical record into an encrypted form. The data processing center 82 also includes means for matching up each copy 108*a* with its corresponding request 94, such as by human intervention or by an electronic processor. The data processing center 82 will typically include a bar code reader or other means for interpreting an identification code associated with each medical record copy received as part of a subsystem for associating the medical record with its corresponding request.

The data processing center 82 advantageously includes storage means, such as one or more magnetic disks or tapes, volatile and nonvolatile memory devices, optical storage devices, and the like for storing the encrypted copy 108*b* of the medical record, preferably in the form of a searchable digital database for later access and retrieval. In the case where the provider 86 can communicate with the data processing center 82 by means of a provider interface module, the provider 86 may be able to determine whether a requested medical record has already been copied and stored within the digital database. Moreover, the searchable digital database may be made accessible to the provider 86 to allow the provider 86 to quickly pull up a digital copy of a medical record stored therein.

The data processing center 82 includes means for sending an encrypted copy 108*b* of the medical record to the requestor 84 and/or other authorized party 110, such as one or more networked computers. The data processing center may also include means for sending a tangible copy 108*a* of the requested medical record to the requestor 84 or other authorized party 100 such as one or more fax machines or a conventional mail center.

In order to provide the ability for a requestor to periodically check the status of a particular request, a status check module may be provided by the data processing center 82.

The status check module may also allow a requestor to determine if there is a problem or informality that might be causing delay in processing the request, such as a missing authorization, an exorbitant site fee, or the need to supply or obtain additional information.

C. Communication Between Data Processing Center and the Various Parties.

Although FIG. 2 provides a general outline of the inventive systems for processing requests for medical records according to the invention, a more detailed explanation of the manner in which the various parties, entities, or systems advantageously communicate with each other may be helpful to have a fuller appreciation of the intricacies of the inventive systems.

Figure 3:
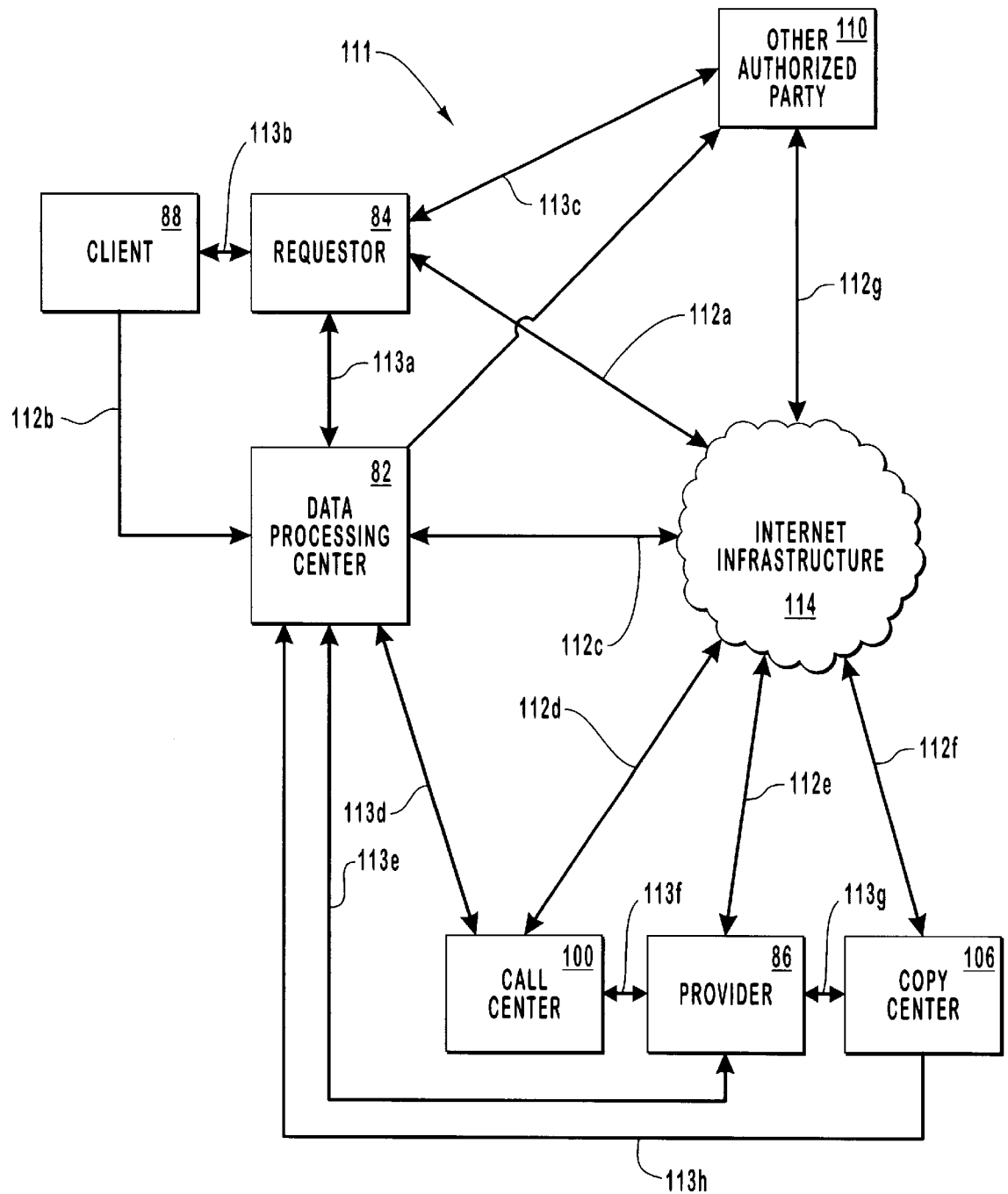
FIG. 3 is a schematic diagram illustrating the exemplary system or network of FIG. 2 employing or including the Internet infrastructure as part of the system or network for processing requests for medical records according to the invention.

As illustrated in FIG. 3, at least some of the communications between the various parties are carried out by means of the Internet, more particularly the Internet infrastructure. As shown in FIG. 3, a communications network 111 is shown that includes the aforementioned data processing center 82, requestor 84, provider 86, client 88, call center 100, copy center 106, and other party 110, which may be linked together by means of communications interfaces 112 between these parties and an Internet infrastructure 114. The Internet links 112 are advantageously provided with firewalls or other secure portals, as well as encryption hardware and software, to prevent unauthorized access to confidential or other sensitive information being shared between the various parties.

In some cases the parties may also communicate by means of direct communication linkages 113 that do not involve the Internet infrastructure 114. Such direct linkages 113 may include, for example, dedicated modem lines, either through hard-wired phone lines or wireless communication pathways, telephones, fax machines, and devices for the manual or verbal sharing of information.

The communications subsystem linking the data processing center 82 and the one or more requestors 84 typically includes an Internet connection, together with one or more direct links. The Internet connection between the requestor 84 and data processing center 82 may be in the nature of a subscription in which the requester 84 is able to log on to a website provided by the data processing center 82. In this scenario, communications between requestor 84 and data processing center 82 will typically be in the form of HTML documents.

Alternatively, the requestor 84 and the data processing center 82 may be connected by an application program interface (API), which involves special software that integrates the existing software for generating requests in the computer system of requestor 84 and the operating system of the data processing center 82. In the case of an API, each requestor 84 could conceivably use its own software when generating the request. The API then converts the request from whatever format is used by a particular requestor 84 into a format that is compatible with the manner in which data are processed by the data processing center 82. Digitally signed authorizations 92 and encrypted copies 108b of medical records (FIG. 2) can also be sent by means of an Internet connection between the requestor 84 and the data processing center 82 (FIG. 3).

In the case where a manually signed authorization 92 is generated, the communication between the requestor 84 and the data processing center 82 may be a fax machine of the requestor 84 connected to the data processing center 82 by means of an Internet connection or a dedicated phone link. A manually signed authorization form 92 may also be sent from the client 88 directly to the data processing center 82 by means of a fax machine, or else it may be faxed from the client 88 to the requestor 84. Thus, in addition to the Internet infrastructure 114, other communication links between the requestor 84 and data processing center 82 may include fax terminals, fax modems, scanners, direct telephone linkages, and the like.

Similar connections between the data processing center and other third parties are within the scope of the invention. These include connections between the data processing center 82 and one or more providers 86, one or more call centers 100, and any other party that may be part of the transaction or process of obtaining a copy of a requested medical record. At present, the communication link between the data processing center 82 and the provider 86 is by means of a fax machine of the provider 86 that is linked by a direct connection to the data processing center 82. Of course, this system may evolve such that the connection between the data processing center 82 and the provider 86 can be wholly electronic such that the request and authorization bundle 98a will be received on a computer of the provider 86 rather than a fax machine.

The communication between the data processing center 82 and the call center 100 may be by means of an Internet connection, one or more direct links, a fax machine, and digitally connected computer systems. There may also be a telephone linkage for verbal communication between a representative of the data processing center 82 and the call center 100.

The communication linkage between the call center 100 and each provider 86 typically will be a direct telephone link because the communication is preferably verbal. Of course, the telephone link may also be wireless or through an Internet telephone system. The communication between the call center 100 and a provider 86 may also include digitized text or image messages including e-mails and HTML documents.

The communication between the provider 86 and the copy center 106 may be computerized and/or comprise human intervention. The communication between the copy center 106 and the data processing center 82 typically will include a fax machine but it may also include a direct computer linkage or Internet connection to send digitized text or image documents, or it may comprise conventional mail. In the case of a tangible copy of a requested medical record 108a, the data processing center 82 or an affiliate will include a scanner or fax machine to convert the tangible copy of the medical record into digitized form.

III. METHODS FOR REQUESTING AND PROVIDING DIGITIZED COPIES OF MEDICAL DOCUMENTS

Figure 4:
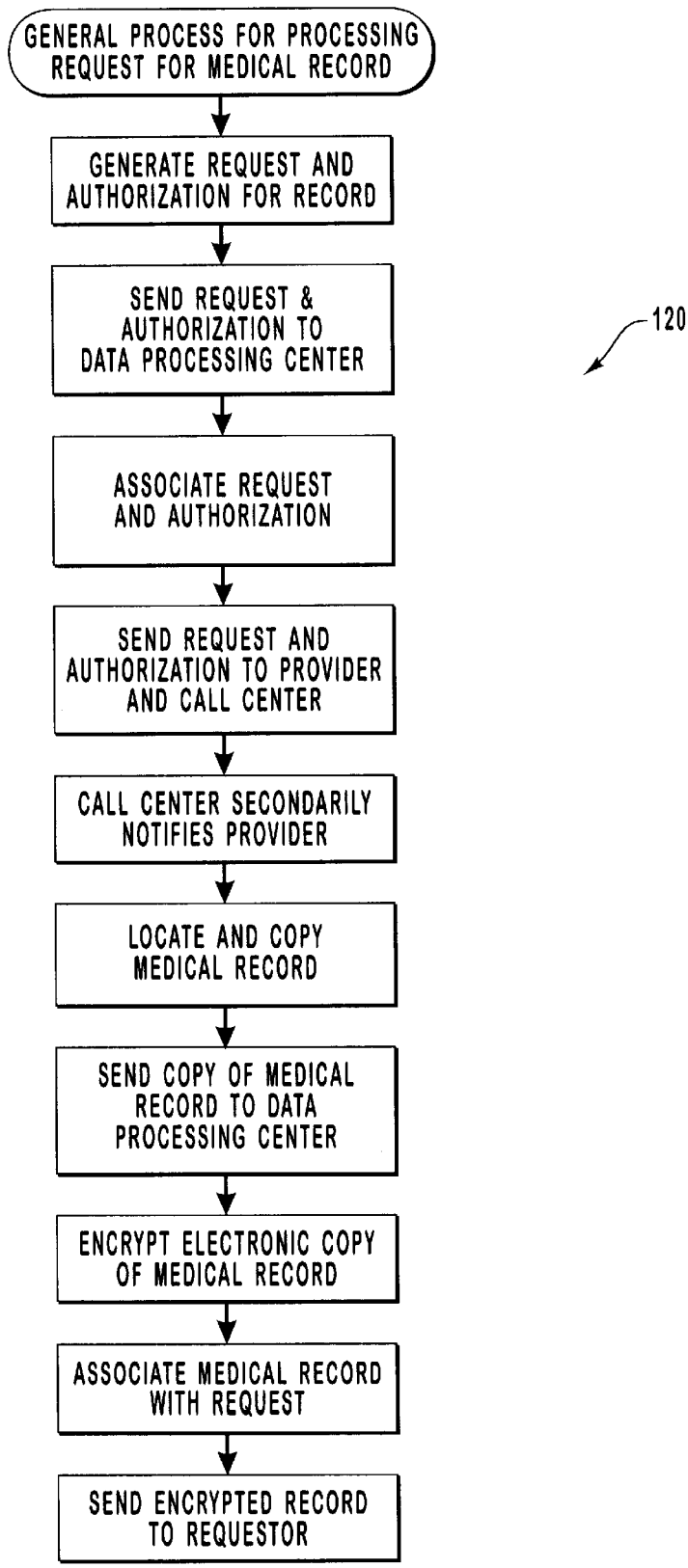
FIG. 4 is a flow diagram depicting an exemplary process by which a request for a medical record may be processed.

FIG. 4 is a flow diagram depicting an exemplary general process 120 by which a request for a medical record may be processed. In a first step, a requestor generates a request for a medical record and then obtains a signed authorization from a person who has a legal right to authorize the release of the record, typically the patient to whom the record pertains or a legal guardian or other person with power of attorney. The requestor then sends the request and authorization to the data processing center. A more precise description of how the requests and authorizations are generated and sent is discussed below.

The data processing center receives and associates the request and its corresponding authorization. Because the data processing center will typically receive numerous requests and authorizations, which are often sent at different times and possibly in different formats, it will be necessary for the data processing center to associate each request with its corresponding authorization. A more detailed description of how the data processing center associates each request with its corresponding authorization is described below.

The data processing center sends the request and authorization to the provider that has access to the requested medical record. At about the same time, the data processing center sends the request and authorization to a call center, which provides secondary notification to the provider that the request and authorization have been sent. The purpose of the secondary notification is to ensure compliance and fast and efficient processing of the request by the provider. A more detailed description of how the request and authorization are sent to the provider and call center, as well as how the call center processes the information and then notifies the provider, is discussed more fully below.

Upon receiving the request and authorization, the provider, affiliate or contracted third party has the responsibility of locating and copying the medical record and sending a copy of the medical record to the data processing center. In most cases, the medical record will be a paper document, typically hand-written, thus requiring the record to be scanned or photocopied rather than being sent directly to the data processing center. On the other hand, digitally stored records can be digitally copied and sent without the need for a copy machine and/or scanner. A more detailed description of the process of locating, copying, and sending the medical record to the data processing center is discussed below.

The data processing center receives the copy of the requested medical record in either tangible or digital form. In the case where the record is in tangible form, the data processing center or an affiliate will scan the document and digitize it. At some point after receiving the medical record, in either tangible or digital form, the data processing center associates the medical record with the request. A more detailed description of the process of associating a medical record with its request and then sending an encrypted medical record or hard copy to the requestor is set forth below.

Finally, the data processing center sends a copy of the requested medical record to the requestor or other authorized party. The data processing center advantageously encrypts the digitized record prior to sending it to the requestor or other authorized party in order to preserve the integrity and/or privacy of the information contained therein. In some cases, the data processing center may send a hard copy of the requested medical record, such as by facsimile or conventional mail. A more detailed description of the process of sending medical records to the requestor is set forth below.

A. Generating and Sending Requests and Authorizations to Data Processing Center.

Figure 5:
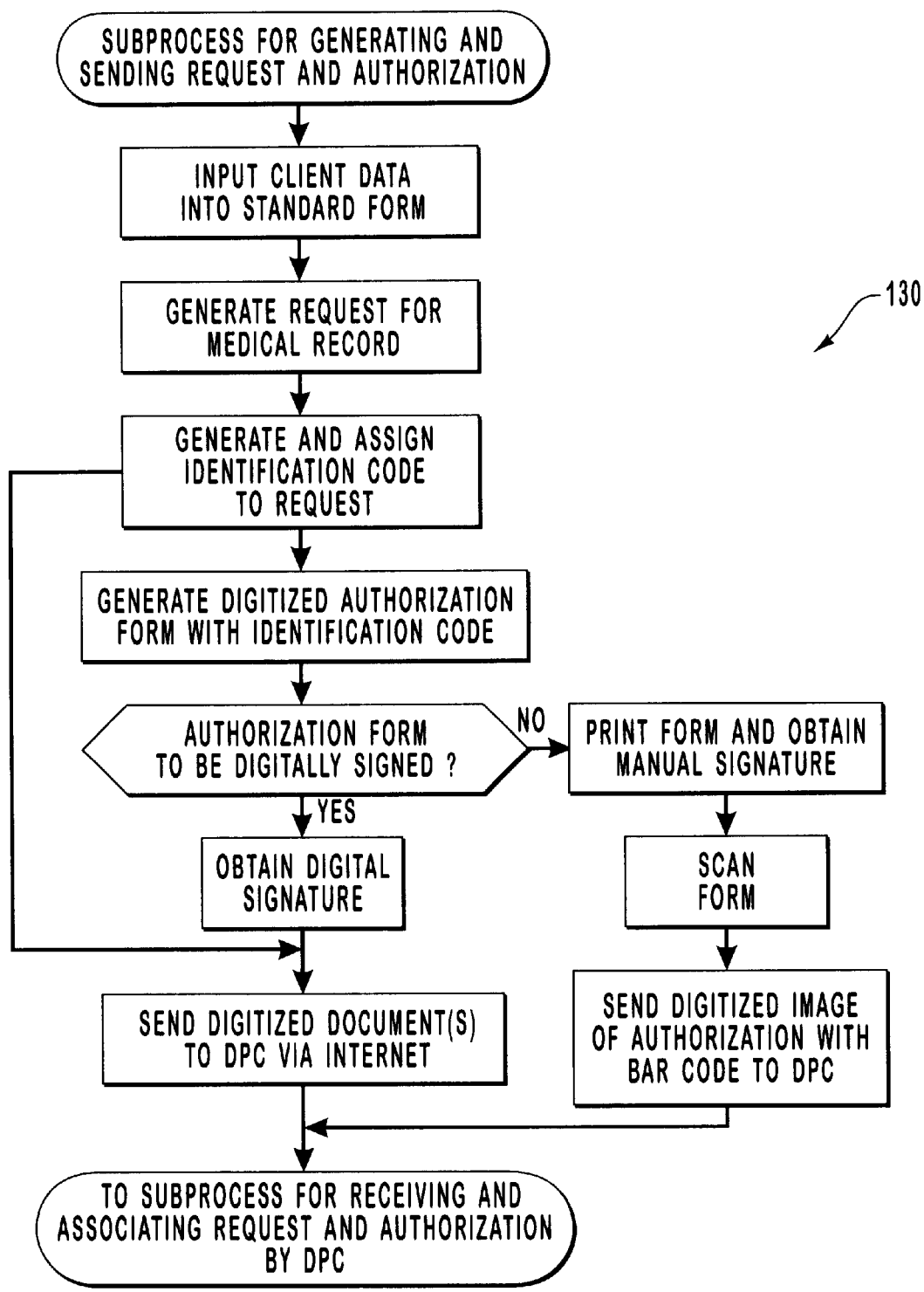
FIG. 5 is a flow diagram depicting an exemplary subprocess for generating and sending a request and corresponding authorization for a medical record to a data processing center.

Following is a more detailed description of the subprocess for generating requests and authorizations by a requestor and receiving and associating the requests and authorizations by the data processing center. FIG. 5 is a flow diagram depicting an exemplary subprocess 130 for generating and sending a request and corresponding authorization for a medical record from a requestor to a data processing center. As more particularly illustrated in FIG. 5, a requestor, prior to generating a request for a medical record, inputs client data into a standard form. The standard form is typically a computerized form visible on the computer screen of the data processor or agent assigned the task of inputting the client data into the standard form. The form may be an HTML document provided by a data processing center web page, or it may be a standard form unique to that requestor that is part of an API system linking the requestor and the data processing center.

After the standard form has been filled out to include all necessary or pertinent client, provider, and record data and the like, a request for one or more medical records is generated. The data processing center generates a unique identification code for that request. The purpose of the identification code is to allow the data processing center to associate each request with its corresponding authorization. The identification code is also used to associate a requested medical records with its corresponding request. The identification code may be generated in any desired manner, such as a serial number. It may comprise a multiple primary key consisting of multiple fields compressed to form a unique identifier.

At about the same time that the request is generated, the requester also generates an authorization form, typically initially in digital form within the computer used to generate the request. The authorization form will be assigned the same or a related identification code that will allow the authorization form and request to be later associated by the data processing center.

The requestor may be advantageously equipped to obtain a digital signature from their client or other person who is legally permitted to sign the authorization form. In such a case, a digital authorization form together with its digitally signed signature will be sent along with the request to the data processing center, preferably via an Internet connection.

Alternatively, in the case where the client of the requestor wishes to manually sign the authorization form, which is typically the case at present, the requestor prints out an authorization form and associated cover sheet with a bar code or other scannable image printed therein representative of the identification code. The requestor will either have the client sign the form in person or else send the authorization form to the client for signature. The manually signed authorization form and cover sheet may be scanned and converted into a digital image, such as by a fax machine that sends the electronic image to the data processing center.

The scanned authorization form and cover sheet are sent to the data processing center, either directly by the client or by way of the requestor. As a practical matter, the step of scanning and sending a digital copy of the manually signed authorization form and cover sheet can be performed in a single step using a fax machine. The client can either fax the signed authorization form and cover sheet directly to the data processing center, or else the client may mail or fax the signed form to the requester, who then faxes the form and cover sheet to the data processing center. Of course, it is certainly possible for the authorization form itself to include a bar code image or other form of the identification code, thus dispensing with the fax cover sheet altogether. The authorization and bar code can be sent as tangible documents to the data processing center, whereupon they are scanned and the bar code read.

Where a facsimile image of the bar code is sent to the data processing center, degradation of bar code quality and/or low resolution may diminish bar code readability. In order to offset possible degradation or low resolution of the bar code image, the data processing center may perform an image enhancement algorithm, such as an algorithm intended to straighten out bar code lines that are no longer straight or to remove or average out noise. In the alternative, or in addition, the bar code may initially include relatively thick lines in order to at least partially offset or dampen the effects of facsimile transmission noise and/or low resolution. The data processing center may scan the bar code at multiple orientations or angles and then compare the different readings in order to confirm a correct reading to a desired certainty level. The fax cover page or authorization may include multiple bar codes representing the same identification code placed at different locations and orientations on the page in an attempt for at least one of said multiple bar codes to overcome nonsystematic noise, degradation or low resolution during facsimile transmission.

The next step is for the data processing center to perform the tasks of receiving and associating each request with its corresponding authorization.

B. Receipt and Association by Data Processing Center of Each Request and Authorization.

Figure 6:
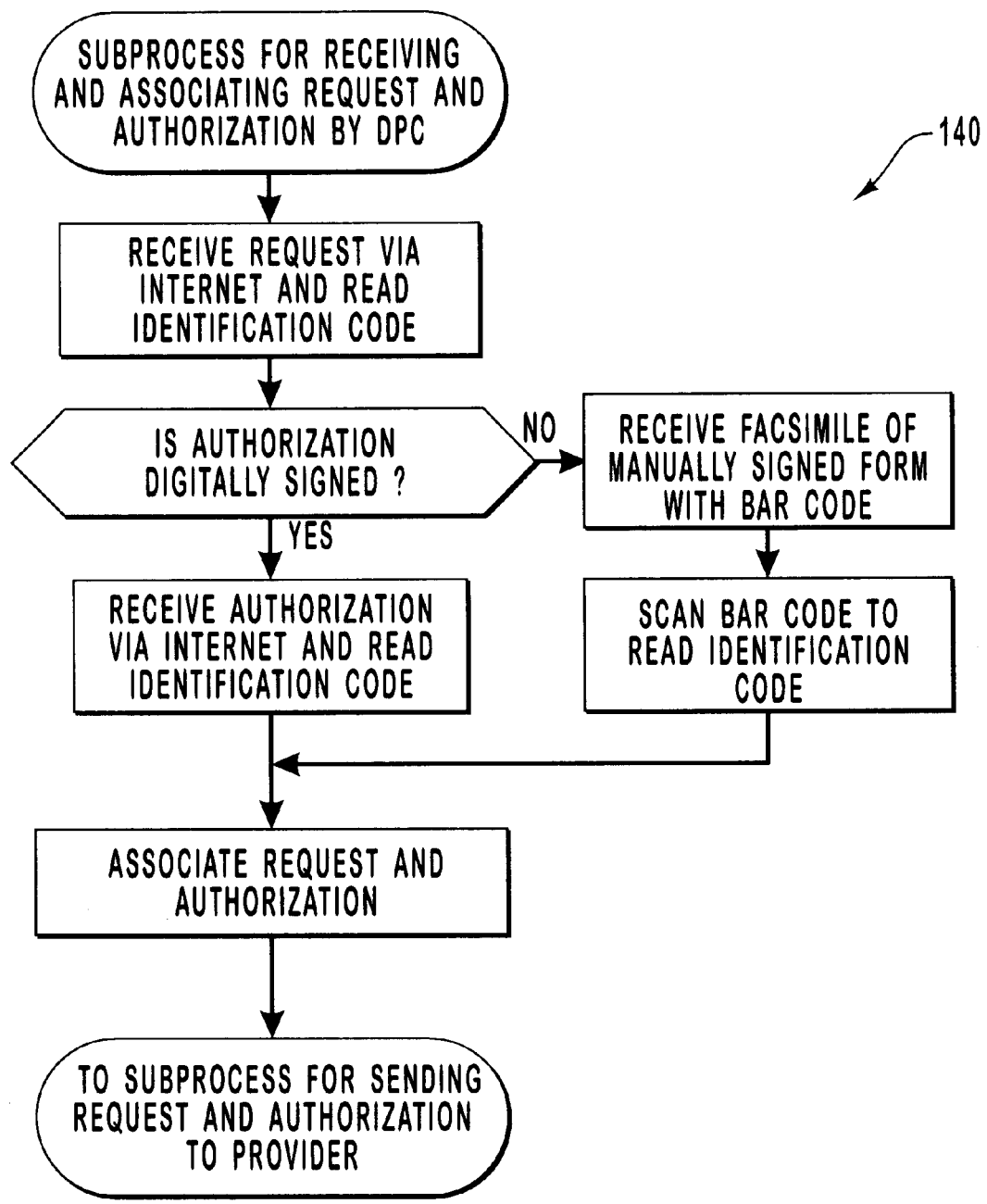
FIG. 6 is a flow diagram depicting an exemplary subprocess for receiving and associating a request and corresponding authorization by a data processing center.

FIG. 6 is a flow diagram depicting an exemplary subprocess 140 for receiving and associating requests with their corresponding authorizations by the data processing center. The data processing center receives each request from the various requesters via an Internet or direct connection and reads the respective identification code relating to each request. Because the requests are typically sent in digitized text format, the data processing center can readily interpret the identification code as a text string. The text string may comprise any string of numbers, letters, and/or other recognizable characters that will advantageously provide each request with a unique identification code (e.g., a serial number or multiple primary key).

In the case where the authorization is digitally signed, the authorization may be sent and received by means of the Internet or direct connection used to send the request. As such, the authorization may also include an identification code as a readable text sequence. If so, the data processing center can immediately compare the identification code of each request with those of each authorization to find a match and thereby associate each request and authorization.

Alternatively, manually signed authorizations are typically scanned and digitized as an image document, such as by means of a fax machine. In this case, the identification code cannot usually be read as a digitized text string. Instead, the identification code will typically be in the form of a bar code or other scannable image representing the identification code assigned to that authorization form. The bar code or other scannable image is then scanned and converted into an identification code by the data processing center, which is then able to compare the respective identification codes of the various authorizations with those of the requests to associate each authorization with its corresponding request. Of course, a text recognition algorithm could be used to read an identification code as a text image.

In many cases, the signed authorization form will be sent by means of a facsimile transmission. To compensate for degradation of the bar code due to data communication noise and low resolution that are typical with fax communications, the bar code may be provided with extra thick lines that are able to average out and compensate for such data transmission noise. In addition to, or instead of, using thicker bar code lines, the bar code scanner (which is typically an optical character recognition-type image scanning system rather than a laser bar code reader typically found in a retail outlet) may advantageously read the bar code in various places and/or at various angles to obtain a number of alternative readings of the same bar code. In connection with this, multiple bar codes may be provided, for example, bar codes at different orientations, to compensate for telecommunications noise in different directions on the page.

Reading a bar code at different places, and/or manners, and/or locations, and/or orientations on the page allows for the ability to confirm whether a particular reading is correct. In most cases, the number of correct readings will exceed the number of incorrect readings, thus providing a test as to whether a particular reading was correct, at least to a certain confidence level. The different readings are tabulated and then compared, and incorrect readings are rejected. The correct reading is identified and then used to associate each authorization with its corresponding request.

The data processing center typically receives manually signed authorization forms as facsimile images using fax receiving software. The fax numbers, direct telephone linkages, or Internet connections through which the faxes are sent and received by the data processing center may advantageously be unique to authorization forms (and exclude other communications, such as the receipt of faxed medical records) to. facilitate the ability to match the authorizations with their respective requests.

In most cases, at least for the time being, the data processing center will not already have a copy of the requested record but will transmit the request and authorization to the appropriate provider. Nevertheless, it may be possible for the data processing center to already have a digitally stored copy of the requested medical record, particularly over time as more medical records are retrieved and stored in digital form. Therefore, it may be advantageous to preliminarily determine whether a record has already been stored in the data processing center or within a databank accessible by the data processing center.

Figure 7:
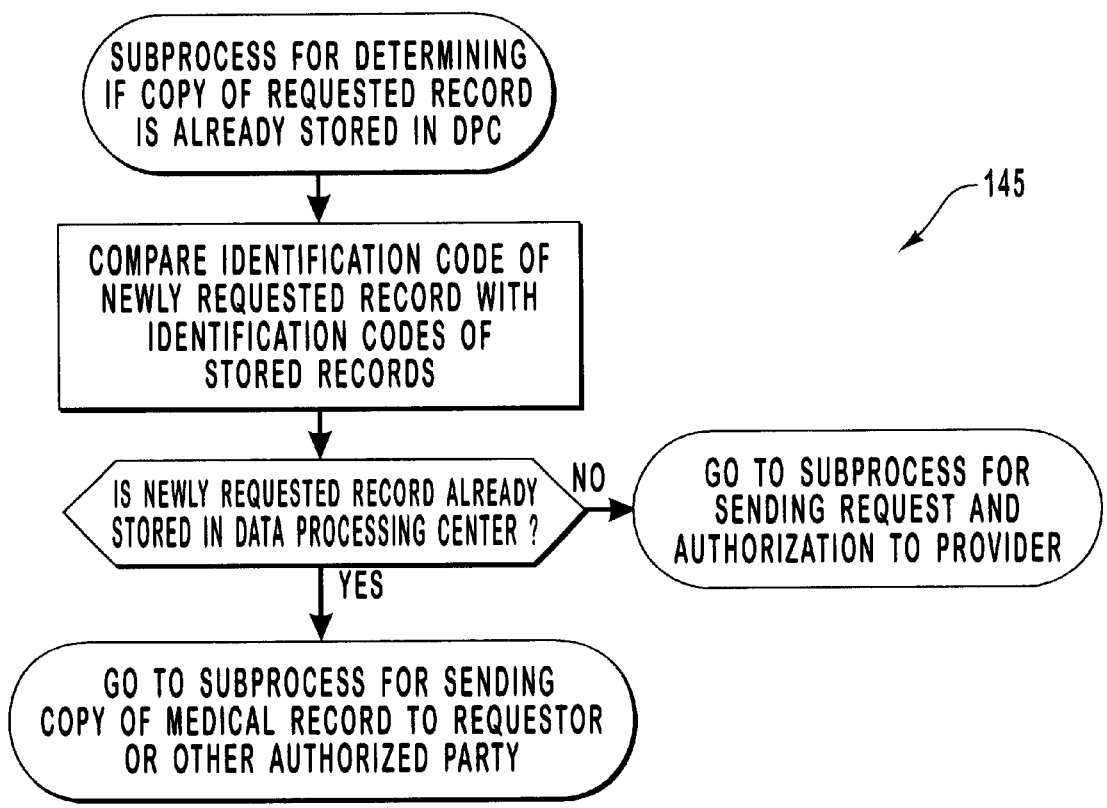
FIG. 7 is a flow diagram depicting an exemplary subprocess for determining if a requested medical record is already stored in the data processing center.

FIG. 7 is a flow diagram depicting an exemplary subprocess 145 for determining if a requested medical record is already stored in the data processing center. As more fully depicted in FIG. 7, subprocesses 145 compares the identification code of a newly requested record (i.e., the identification code of the request for that medical record) with identification codes of medical records already stored within the data processing center. This may be done, for example, by accessing a list of identification codes relating to stored documents, preferably associated with a pointer that assists in retrieving a record stored in an accessible database. Of course, it will be appreciated that it is not necessary for the data processing center to have actually stored digital copies of the requested medical record so long as it can at least identify whether a medical record is digitally stored somewhere and then access the record in some manner. In such a scenario, the data processing center can then take appropriate measures to obtain a copy of the digital record, which would streamline the process of obtaining the record versus actually obtaining the record from a provider. An advantage of using a multiple primary key as the identification code is that it may include an embedded code that is unique to an already digitally stored medical record, thus facilitating subprocess 145.

If the data processing center is able to immediately obtain a digital copy of the requested medical record, it can bypass the process of contacting the provider and instead go immediately to the subprocess for sending the digitized medical record to the requestor or other authorized party. On the other hand, if the medical record is not digitally stored or otherwise accessible to the data processing center, the data processing center will then go to the subprocess for sending the request and authorization to the provider.

C. Sending Requests and Authorization From the Data Processing Center to a Provider.

Figure 8:
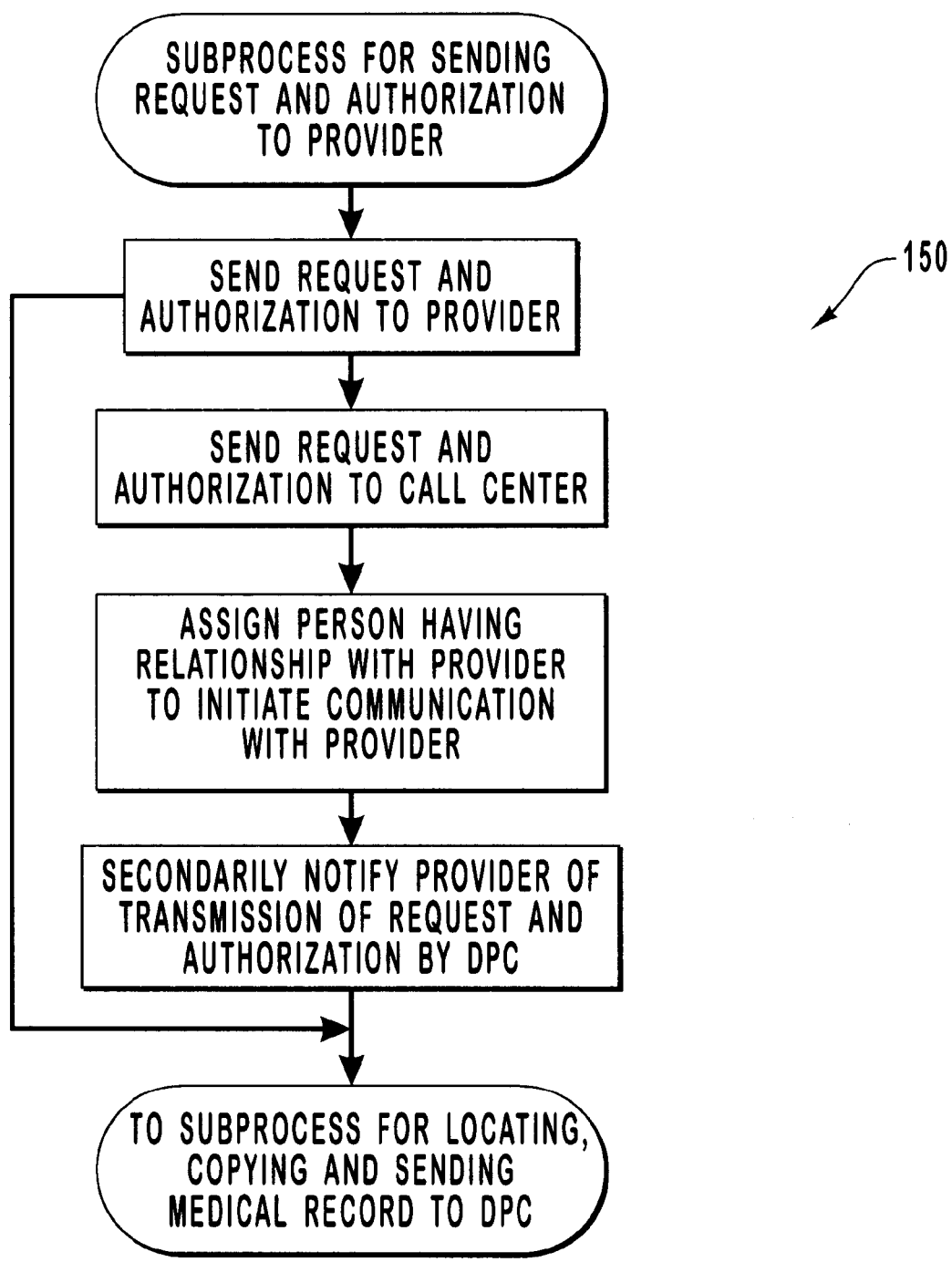
FIG. 8 is a flow diagram depicting an exemplary subprocess for sending a request and authorization from a data processing center to a provider.

FIG. 8 illustrates an exemplary subprocess for sending requests and authorizations from the data processing center to a provider. As more fully illustrated in FIG. 8, the subprocess 150 includes a first step of sending a request and its corresponding authorization to one or more providers who are in possession of or have access to the requested medical record. The request and authorization are typically sent to the provider as a fax communication, typically together with a fax coversheet that will be sent along with the copy of the medical record back to the data processing center. The fax coversheet will include an identification code that permits the data processing center to associate the copied medical record with its corresponding request. Alternatively, the request and authorization may be sent digitally to a computer of the provider.

To ensure provider compliance with the request, the request and authorization may also be sent nearly simultaneously to a call center, which assigns each request to a person who initiates a telephone call or other real-time "live" communication with the provider. The person assigned the task of calling and notifying a provider that a request and authorization has been (or will be) sent will typically be a person who has an existing relationship with that provider. It has been found that providers are more likely to respond favorably when contacted by a person with whom they have a preexisting relationship. For best results, the communication initiated by the call center to the provider will occur concurrently with receipt of the request and authorization by the provider, typically by means of a fax communication from the data processing center to the provider. Thus, the call center can notify the provider that a request is presently coming over the fax machine and can confirm that the provider has received the request and will act on and carry out the request. The communication between the call center and the provider may be referred to as a secondary communication, while the communication from the data processing center to the provider is the primary communication.

After the provider has received the request and authorization, typically along with a secondary communication from a call center, the next step is locating, copying, and sending a copy of the medical record to the data processing center.

D. Retrieving, Copying and Sending Requested Medical Records to the Data Processing Center.

Figure 9:
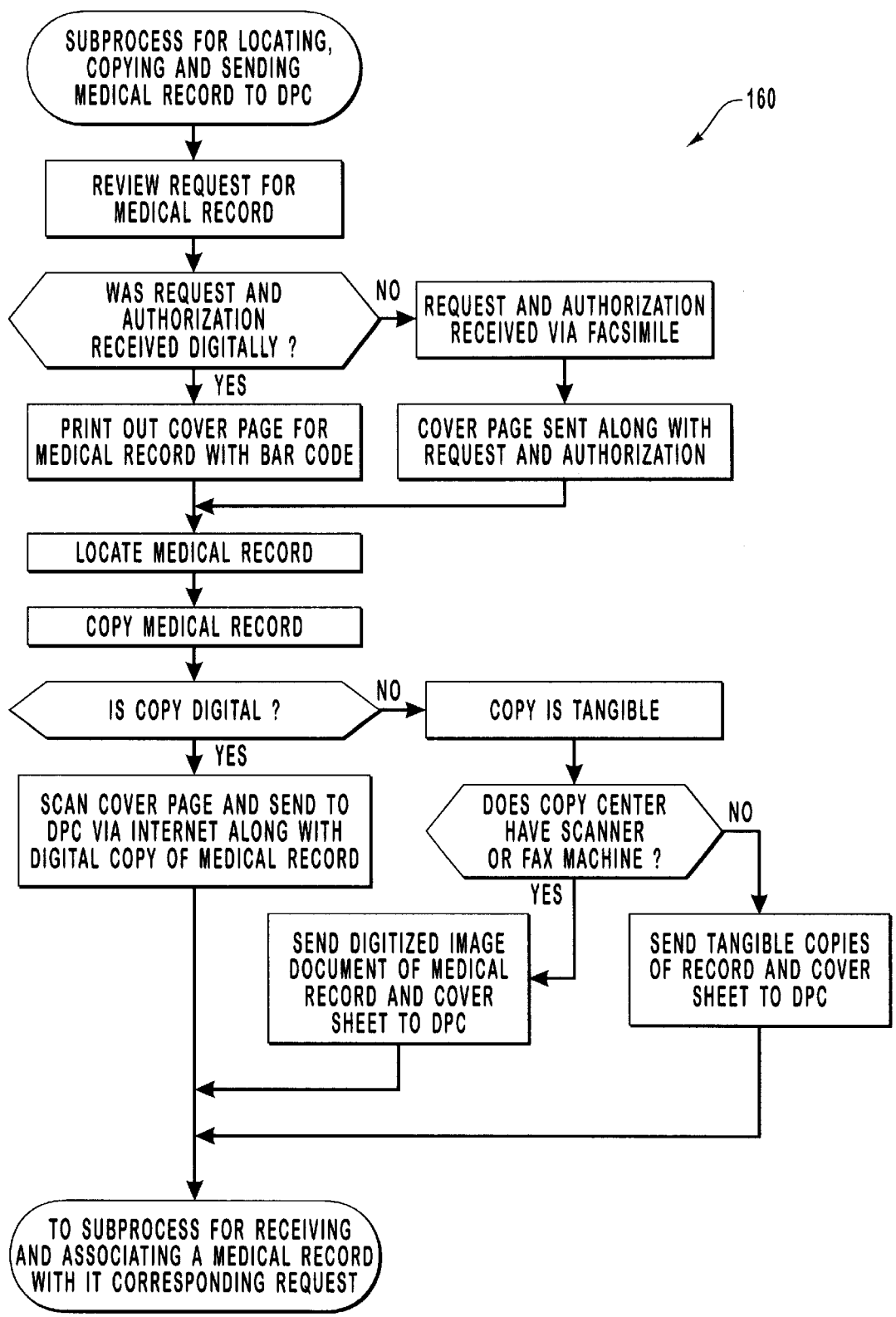
FIG. 9 is a flow diagram illustrating an exemplary subprocess for locating, copying, and sending a requested medical record to a data processing center.

FIG. 9 is a flow diagram depicting an exemplary subprocess 160 for retrieving and copying a requested medical record by a provider, as well as sending a copy of the requested record to the data processing center. As more particularly shown in FIG. 9, this subprocess typically requires human intervention because most medical records presently are in tangible, handwritten form. In a first step, the provider, employee, or agent of the provider reviews a request for a medical record and determines where to locate the medical record. In some cases, the request may either be sent by fax or by a digitized document received by a computer, such as a text document. If the document was received digitally, the provider, employee, or agent will typically print out a cover page for the medical record that includes a bar code or other scannable image that will assign an identification code to the copied medical record. If the request was received via facsimile, the facsimile communication from the data processing center will typically include a copy of the cover page to be physically associated with the copy of the medical record. The same strategies discussed above may be employed in order to offset or account for possible bar code degradation or low resolution resulting from facsimile transmission.

Medical records are typically stored in large filing rooms and must be pulled by hand, checked out, copied, and then returned to their proper location. The provider or agent of the provider or requestor locates and retrieves the requested medical record and takes it to a copy center. The copy center may make a photocopy or digital copy of the requested medical record, such as by scanning the record. When a digital copy of the record is made, it may be advantageous to simultaneously scan the cover page with the bar code or other scannable image to physically associate the medical record with its assigned identification code. In the case where the request and authorization are received by the provider in digital form, it will not usually be necessary for the copy center to scan the cover page since it will also already exist in digital form.

At present, it will be more common for the medical record to simply be photocopied by the provider and then physically associated with the cover page. If the copy center has a scanner, the requested medical record and associated cover sheet may be scanned and sent to the data processing center as a digital image document. If the copy center has a fax machine, the requested medical record and associated cover sheet may be faxed directly to the data processing center, which receives the faxed images within a fax modem as a digitized image, typically as a tagged image file format (.tiff) image. Alternatively, the copy center may simply send a physical copy of the copied medical record and associated cover sheet to the data processing center, which then scans the documents and converts them into digitized images. At this point, the medical record will then be associated with its corresponding request, possibly after first being encrypted.

E. Receiving and Associating Medical Records With its Corresponding Request by the Data Processing Center.

Figure 10:
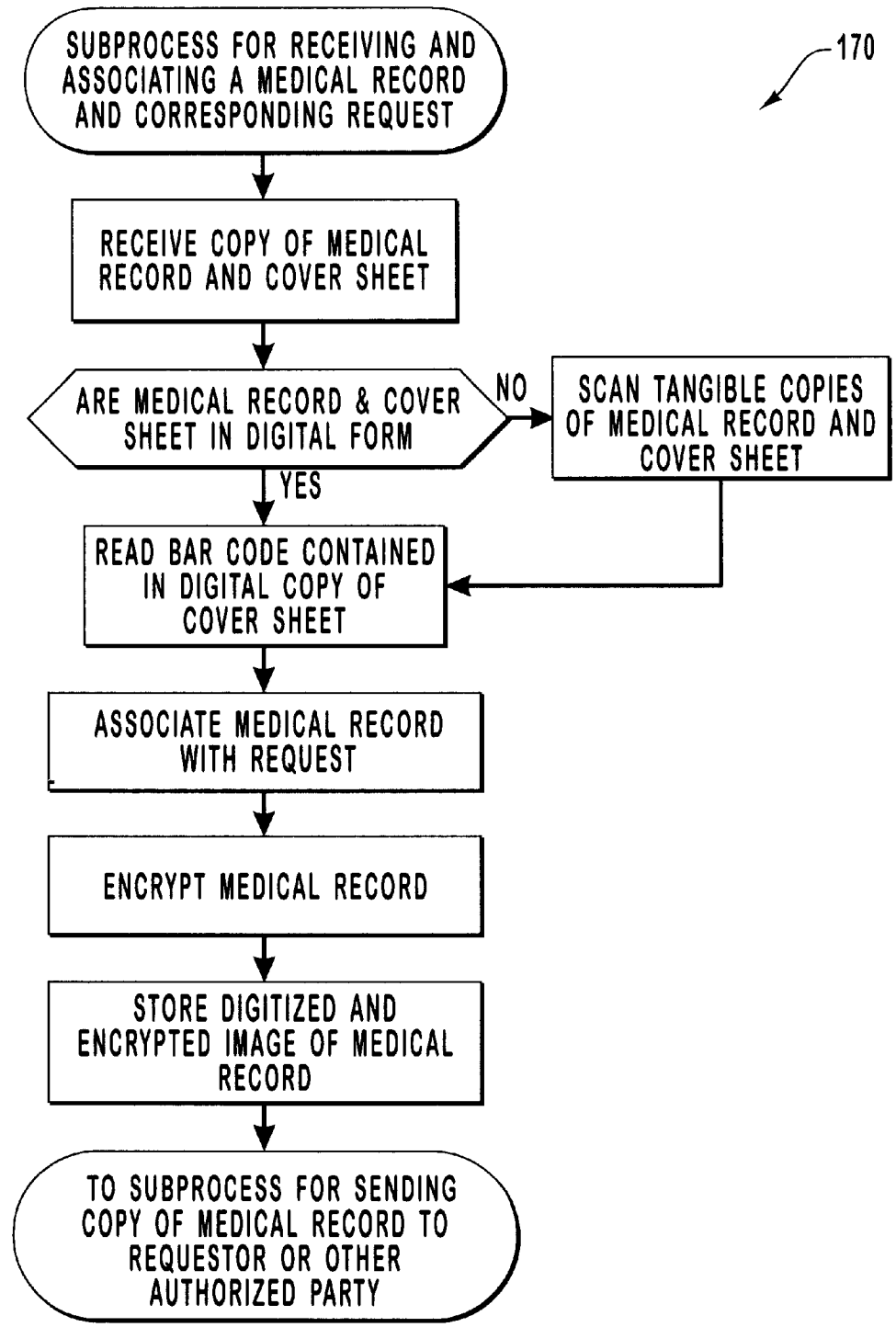
FIG. 10 is a flow diagram illustrating an exemplary subprocess for receiving and associating a medical record with its corresponding request by a data processing center.

FIG. 10 is a flow diagram illustrating an exemplary subprocess 170 for receiving and associating a medical record with its corresponding request by the data processing center. As more particularly depicted in FIG. 10, the data processing center receives a copy of the requested medical record together with a cover sheet that includes a corresponding identification code. If the medical record and cover sheet are in the form of a digitized image, the data processing center can read the identification code using an optical bar code reader or character recognition reader. The same strategies discussed above may employed to ensure an accurate reading of the bar code in order for the data processing center to accurately ascertain the identification code associated with each copy of the requested medical records. If the cover sheet is a digital text document, the identification code may be read directly by the data processing center.

If the provider simply sends a hard copy of the medical record and cover sheet to the data processing center, these will be scanned and converted into a digital image such as a tiff file. The bar code or other scannable image may be read in the same manner as described above, such as by means of a bar code reader or character recognition.

After the identification code has been read, the digital medical record is associated with its corresponding request by means of comparing their respective identification codes and then stored within an appropriate database, such as a database within the data processing center or a remote database.

To preserve the confidentiality of a digital medical record, it may advantageously be encrypted prior to or after being initially stored using encryption processes known in the art. A presently preferred encryption algorithm involves "hash encryption" using both public and private encryption keys together with one or more "X-or" functions. Encrypting a medical record not only prevents unauthorized access of the medical record by third parties, it may also serve to prevent unauthorized alteration or obliteration of the medical record, such as by an unscrupulous salesman who wants to remove sensitive information that may otherwise block a transaction from going forward.

F. Sending Copies of Requested Medical Records by the Data Processing Center.

Figure 11:
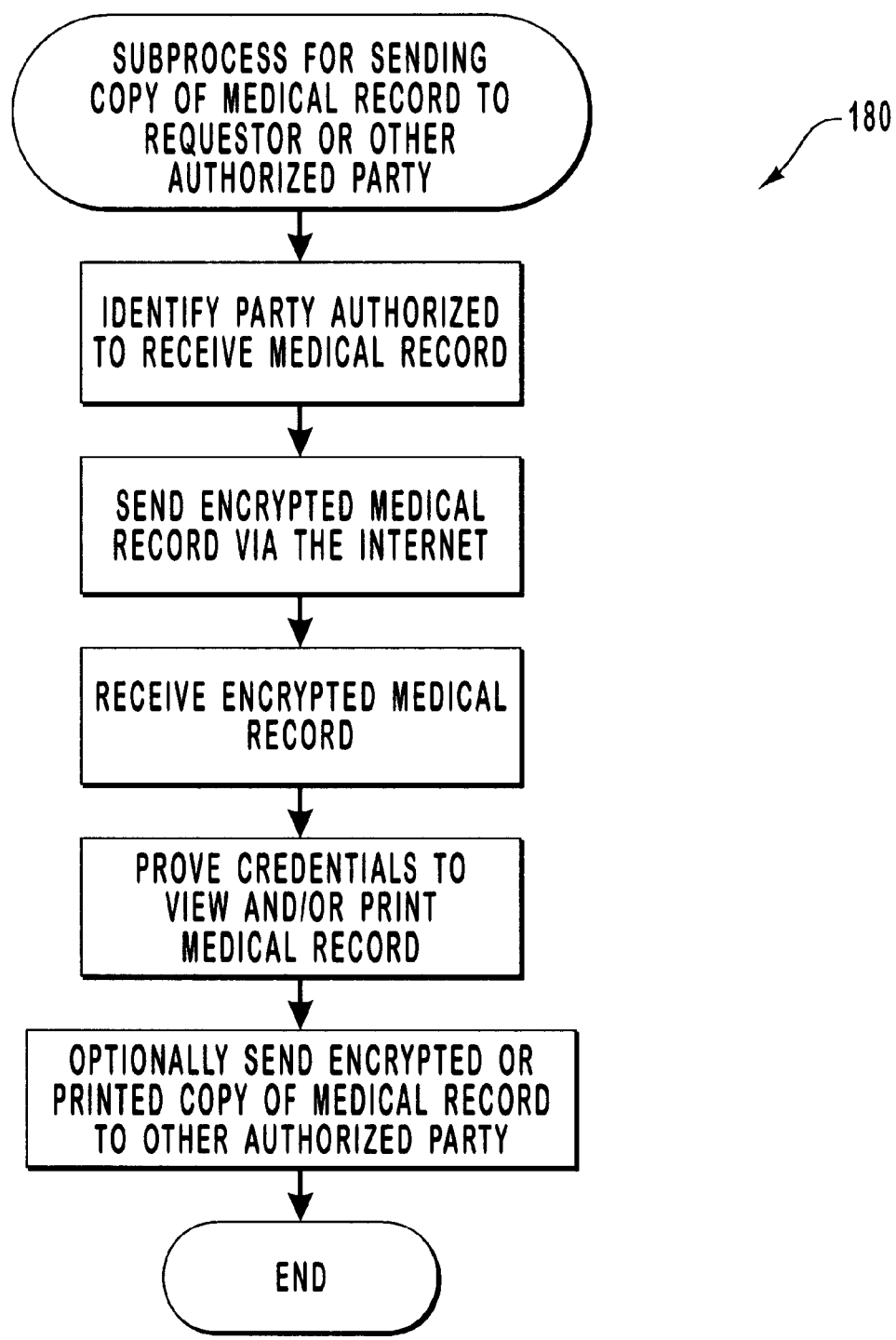
FIG. 11 is a flow diagram illustrating an exemplary subprocess for sending a copy of a medical record to the requester or other authorized party.

FIG. 11 is a flow diagram illustrating an exemplary subprocess 180 for sending a copy of a requested medical record to the requestor or other authorized party. First, the data processing center must identify the party or parties who are authorized to receive the requested medical record. This may be done, for example, by simply identifying the party that generated the original request. In addition, the request and/or authorization may name other authorized parties to which the record may be sent, either in digitized or tangible form.

If the requestor or other authorized party is to receive a digital copy of the medical record, the medical record is preferably sent in encrypted form to preserve its confidentiality and prevent unauthorized alteration of the document. The digital copy of the medical record will advantageously be sent by means of an Internet connection from the data processing center to the requestor or other authorized party. This may be done, for example, by means of a direct subscription link between a requestor and a web page of the data processing center, or by means of an API system as described above, or by means of an e-mail or attachment thereto.

In the case of an encrypted image, appropriate encryption software may be necessary to access or view the medical record, typically software that does not provide the ability to readily edit or alter the image. Moreover, the party receiving the digital image of the medical record may advantageously be required to provide credentials to view and/or print the medical record. The medical record may be sent by the requestor to another authorized party, or else the data processing center may directly send multiple copies to multiple parties.

Although the foregoing processes and systems were described in terms of processing a request for a medical record, it should be understood that such processes and systems may be readily and easily adapted for use in obtaining copies of other types of records, including but not limited to, police records, billing records, pharmacy records, claims histories, fire reports, tax returns, government documents, documents used in litigation, subpoenas, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. In a data processing center, included in a system that also includes one or more requestors of records and a plurality of providers that generate or have custody of records, a method for processing requests for records comprising:

receiving from a requestor a request for a record in the custody of a provider;

receiving from the requestor or other party an authorization for release of the requested record;

associating the request received from the requestor with the authorization received from the requester or other party from among other authorizations and requests received by the data processing center by comparing and finding a relationship between identifying information associated with the request and identifying information associated with the authorization;

identifying a provider from among other providers that has custody of the requested record;

transmitting the request and authorization to the provider;

receiving a copy of the requested record together with identifying information associated therewith;

associating the copy of the requested record with the request from among other copies and requests received by the data processing center by comparing and finding a relationship between the identifying information associated with the copy of the requested record and the identifying information associated with the request;

storing a digital copy of the requested record; and transmitting a copy of the requested record to a party authorized to receive the copy, wherein the data processing center comprises one or more computers and wherein at least a portion of the information received and transmitted by the data processing center is communicated through the Internet.

2. A method as recited in claim 1, wherein the data processing center receives the request in digital form.

3. A method as recited in claim 2, wherein the data processing center receives the request as an HTML document that includes at least one of text or graphic information.

4. A method as recited in claim 2, wherein the data processing center receives the request by means of an application program interface linking the data processing center with a computer system of the requestor, the request including at least one of text or graphic information.

5. A method as recited in claim 1, wherein the data processing center receives the authorization in digital form together with a digital signature.

6. A method as recited in claim 1, wherein the data processing center receives the authorization as facsimile information representative of a signed tangible authorization form together with facsimile information representative of a bar code graphically depicting the identifying information associated with the authorization, wherein the data processing center reads the facsimile information representative of the bar code as part of associating the authorization with the request.

7. A method as recited in claim 6, wherein the data processing center enhances the bar code image using an image enhancement algorithm.

8. A method as recited in claim 6, wherein the data processing center scans the facsimile information representative of the bar code multiple times and in different orientations in order to confirm a correct reading of the bar code.

9. A method as recited in claim 6, wherein the bar code received by the data processing center includes bar code lines having thicknesses so as to at least partially decrease degradation of bar code quality resulting from facsimile transmission.

10. A method as recited in claim 6, wherein the authorization received by the data processing center includes multiple bar codes associated therewith in different locations and orientations so as to at least partially decrease degradation of bar code quality of at least one of the bar codes resulting from facsimile transmission, each of the bar codes graphically depicting the identification code associated with the authorization.

11. A method as recited in claim 1, wherein the data processing center transmits the request and authorization to a computer system of the provider together with identifying information to be associated with the copy of the requested record.

12. A method as recited in claim 1, wherein the data processing center transmits the request and authorization to the provider as facsimile information representative of the request and authorization together with facsimile information representative of a bar code graphically depicting identifying information to be associated with the copy of the requested record.

13. A method as recited in claim 12, wherein upon receiving the copy of the requested record the data processing center reads the bar code graphically depicting the identifying information associated with the copy of the requested record as part of associating the copy of the record with the request.

14. A method as recited in claim 13, wherein the data processing center enhances the bar code image using an image enhancement algorithm.

15. A method as recited in claim 1, further including the act of transmitting the request to a call center at approximately the same time that the request is transmitted to the provider.

16. A method as recited in claim 15, wherein the request is assigned to a person having a pre-existing relationship with the provider having access to the requested record.

17. A method as recited in claim 1, wherein the data processing center receives the copy of the requested record as digital graphic information representative of the requested record.

18. A method as recited in claim 1, wherein the data processing center accesses an electronic database of the provider containing the requested record.

19. A method as recited in claim 1, wherein the data processing center performs an encryption process on a digital copy of the requested record in order to protect private information contained in the requested record.

20. A method as recited in claim 1, wherein the copy of the requested record is sent to the party authorized to receive the record as at least one of a facsimile, a tangible copy, or an encrypted digital copy.

21. A method as recited in claim 1, wherein any nonencrypted digital copies of the requested record are deleted from the data processing center.

22. A method as recited in claim 1, wherein the method is repeated for additional requests for other records.

23. A method as recited in claim 22, wherein the method further comprises the data processing center receiving at least one request from at least one additional requestor and at least one copy of a requested record from at least one additional provider.

24. A method as recited in claim 22, wherein digital copies of the additional requested records are stored within an electronic database accessible to the data processing center.

25. A method as recited in claim 24, further comprising the steps of determining whether a subsequently requested record has been previously stored within the electronic database, obtaining a digital copy of the subsequently requested record from the database, and sending the digital copy or a tangible copy of the digital copy to an authorized party.

26. A method as recited in claim 1, wherein the requested record includes at least one medical record.

27. A method as recited in claim 1, wherein the requested record is at least one of a police record, a billing record, a subpoena, an insurance claim history, a fire report or a pharmacy record.

28. A computerized system comprising means for implementing the method recited in claim 1.

29. A computer-readable medium having computer-executable instructions for instructing a data processing center to perform the acts of:
   receiving from a requestor a request for a record in the custody of a provider;
   receiving from the requestor or other party an authorization for release of the requested record;
   associating the request received from the requestor with the authorization received from the requestor or other party from among other authorizations and requests received by the data processing center by comparing and finding a relationship between identifying information associated with the request and identifying information associated with the authorization;
   identifying a provider to from among other providers that has custody of the requested record;
   transmitting the request and authorization to the provider;
   receiving a copy of the requested record together with identifying information associated therewith;
   associating the copy of the requested record with the request from among other copies and requests received by the data processing center by comparing and finding a relationship between the identifying information associated with the copy of the requested record and the identifying information associated with the request;
   storing a digital copy of the requested record; and
   transmitting a copy of the requested record to a party authorized to receive the copy.

30. A computer-readable medium as defined in claim 29, father having computer-executable instructions for enhancing a bar code image using an image enhancement algorithm.

31. A computer-readable medium as defined in claim 29, father having computer-executable instructions for accessing an electronic database of the provider containing the requested record.

32. A computer-readable medium as defined in claim 29, father having computer-executable instructions for encrypting a digital copy of the requested record.

33. A computer-readable medium as defined in claim 32, father having computer-executable instructions for deleting any nonencrypted digital copies of the requested record from the data processing center.

34. A data processing center, included in a system that also includes one or more requestors of records and a plurality of providers that generate or have custody of records, the data processing center having one or more modules for carrying out one or more of the acts comprising:
   receiving from a requestor a request for a record in the custody of a provider;
   receiving from the requestor or other party an authorization for release of the requested record;
   associating the request received from the requester with the authorization received from the reguestor or other party from among other authorizations and requests received by the data processing center by comparing and finding a relationship between identifying information associated with the request and identifying information associated with the authorization;
   identifying a provider from among other providers that has custody of the requested record;
   transmitting the request and authorization to the provider;
   receiving a copy of the requested record together with identifying information associated therewith;

associating the copy of the requested record with the request from among other copies and requests received by the data processing center by comparing and finding a relationship between the identifying information associated with the copy of the requested record and the identifying information associated with the request;

storing a digital copy of the requested record; and transmitting a copy of the requested record to a party authorized to receive the copy, wherein the data processing center comprises one or more computers and wherein at least a portion of the information received and transmitted by the data processing center is communicated through the Internet.

35. A data processing center as defined in claim 34, the data processing center having one or more modules for carrying out the act of receiving the request in digital form.

36. A data processing center as defined in claim 34, the data processing center having one or more modules for receiving the request as an HTML document that includes at least one of text or graphic information.

37. A data processing center as defined in claim 34, the data processing center having one or more modules for receiving the request by means of an application program interface linking the data processing center with a computer system of the requestor, the request including at least one of text or graphic information.

38. A data processing center as defined in claim 34, the data processing center having one or more modules for receiving the authorization in digital form together with a digital signature.

39. A data processing center as defined in claim 34, the data processing center having one or more modules for receiving the authorization as facsimile information representative of a signed tangible authorization form together with facsimile information representative of a bar code graphically depicting the identifying information associated with the authorization, wherein the data processing center reads the facsimile information representative of the bar code as part of associating the authorization with the request.

40. A data processing center as defined in claim 34, the data processing center having one or more modules for transmitting the request and authorization to a computer system of the provider together with identifying information to be associated with the copy of the requested record.

41. A data processing center as defined in claim 34, the data processing center having one or more modules for transmitting the request and authorization to the provider as facsimile information representative of the request and authorization together with facsimile information representative of a bar code graphically depicting identifying information to be associated with the copy of the requested record.

42. A data processing center as defined in claim 34, the data processing center having one or more modules for assigning the request to a person having a pre-existing relationship with the provider having access to the requested record.

43. A data processing center as defined in claim 34, the data processing center having one or more modules for receiving the copy of the requested record as digital graphic information representative of the requested record.

44. A data processing center as defined in claim 34, the data processing center having one or more modules for performing an encryption process on a digital copy of the requested record and to delete any nonencrypted digital copies of the requested record from the data processing center.

45. A data processing center as defined in claim 34, the data processing center having one or more modules for sending the copy of the requested record to the party authorized to receive the record as at least one of a facsimile, a tangible copy, or an encrypted digital copy.

* * * * *

UNITED STATES PATENT AND TRADEMARK OFFICE
CERTIFICATE OF CORRECTION

PATENT NO. : 6,651,060 B1
DATED : November 18, 2003
INVENTOR(S) : Harper et al.

It is certified that error appears in the above-identified patent and that said Letters Patent is hereby corrected as shown below:

<u>Title page,</u>
Item [56], References Cited, U.S. PATENT DOCUMENTS, after "5,552,901 A 9/1996" please replace "Williams" with -- Kikuchi et al. --
Item [57], ABSTRACT,
Line 4, after "requests," replace "requesters" with -- requestors --

<u>Column 1,</u>
Line 8, after "assisting a" replace "requester" with -- requestor --
Line 15, replace "requester" with -- requestor --
Line 23, replace "requesters" with --requestors--
Line 27, replace "filling" with -- filing --
Line 37, replace "requester" with -- requestor --

<u>Column 2,</u>
Line 9, replace "requester." with -- requestor. --
Line 10, replace "requesters" with -- requestors --

<u>Column 3,</u>
Line 6, after "Typical" replace "requesters" with -- requestors --

<u>Column 4,</u>
Line 50, replace "requester" with -- requestor --

<u>Column 5,</u>
Line 26, replace "requesters" with -- requestors --

<u>Column 6,</u>
Line 26, replace "requester" with -- requestor --
Line 61, replace "requesters" with -- requestors --

<u>Column 16,</u>
Line 15, replace "requester" with -- requestor --
Line 47, replace "requester" with -- requestor --

<u>Column 17,</u>
Line 17, replace "requesters" with -- requestors --

UNITED STATES PATENT AND TRADEMARK OFFICE
CERTIFICATE OF CORRECTION

PATENT NO.    : 6,651,060 B1
DATED         : November 18, 2003
INVENTOR(S)   : Harper et al.

It is certified that error appears in the above-identified patent and that said Letters Patent is hereby corrected as shown below:

Column 18,
Line 14, after "records)" replace "to." with -- to --

Column 20,
Line 49, replace "tiff file" with -- .tiff file --

Column 21,
Line 66, replace "requester" with -- requestor --

Column 24,
Line 17, after "provider" remove "to"
Line 32, replace "father" with -- further --
Lines 36, 40 and 43, replace "father" with -- further --
Line 55, replace "requester" with -- requestor --
Line 56, replace "reguestor" with -- requestor --

Signed and Sealed this

Sixth Day of April, 2004

JON W. DUDAS
*Acting Director of the United States Patent and Trademark Office*